United States Patent [19]
Cooper et al.

[11] Patent Number: 5,684,580
[45] Date of Patent: Nov. 4, 1997

[54] HYDROCARBON ANALYSIS AND CONTROL BY RAMAN SPECTROSCOPY

[75] Inventors: John B. Cooper, Virginia Beach, Va.; Philip E. Flecher, Jr., Ormond Beach, Fla.; William T. Welch, Ashland, Ky.

[73] Assignee: Ashland Inc., Ashland, Ky.

[21] Appl. No.: 432,559

[22] Filed: May 1, 1995

[51] Int. Cl.$^6$ .................................................. G01N 21/65
[52] U.S. Cl. .................................................. 356/301
[58] Field of Search .................................................. 356/301

[56] References Cited

U.S. PATENT DOCUMENTS

| | | | |
|---|---|---|---|
| 2,527,121 | 10/1950 | Dudenbostel, Jr. | |
| 2,527,122 | 10/1950 | Heigl et al. | |
| 3,371,574 | 3/1968 | Dwyer | |
| 4,707,603 | 11/1987 | Miemelä et al. | 250/339 |
| 4,963,745 | 11/1990 | Maggard | 250/343 |
| 4,994,671 | 2/1991 | Safinya et al. | 250/255 |
| 5,112,127 | 5/1992 | Carrabba et al. | 356/301 |
| 5,121,337 | 6/1992 | Brown | 364/498 |
| 5,139,334 | 8/1992 | Clarke | 356/301 |
| 5,145,785 | 9/1992 | Maggard et al. | 436/8 |
| 5,190,882 | 3/1993 | Schulz et al. | 436/139 |
| 5,225,679 | 7/1993 | Clarke et al. | 250/343 |
| 5,243,546 | 9/1993 | Maggard | 364/571.02 |
| 5,262,644 | 11/1993 | Maguire | 250/339 |
| 5,266,800 | 11/1993 | Mullins | 250/256 |
| 5,348,645 | 9/1994 | Maggard et al. | 208/209 |
| 5,349,188 | 9/1994 | Maggard | 250/339 |
| 5,349,189 | 9/1994 | Maggard | 250/339.07 |
| 5,362,965 | 11/1994 | Maggard | 250/339.12 |
| 5,370,790 | 12/1994 | Maggard et al. | 208/142 |

OTHER PUBLICATIONS

"Fiber Optic Raman System for On–Line Process Control of a Petroleum Pipeline" by M. L. Myrick and S. M. Angel; Univ. of South Carolina.

"U. S. Reformulated Gasoline Rule Complex Confusing", Annek. Rhodes; Oil & Gas Journal, Jan. 7, 1994.

"Natural Gas & Refined Products", Jane B. Hooper; Anal. Chem., vol. 65, #12, Jun. 15, 1993, pp. 189R–192R.

"A Comparison of Methods to Determine Benzene in Gasoline Boiling Range Material"; R.E. Pauls et al; Journal of Chromatographic Science, vol. 30; Jan. 1992; pp. 32–39.

"Quantative Analysis of Liquid Fuel Mixtures with the Use of Fourier Transform near IR Roman Spect."; M.B. Seasholtz. et al.; Applied Spic., vol. 43, #6; 1989; pp. 1067–1072.

"Determination of Gas Oil Octane Number & Octane Index Using Near–Infared Fourier Transform Raman Spect."; Kenneth P.J. Williams and Aries et al.; Anal. Chem., vol. 62, #23; Dec. 1, 1990.

"Near Infrared Raman Spectroscopy of Liquids & Solids with a Fiber–Optic Sampler, Diode Laser, & CCD Detector"; C.D. Allred & R.L. McCrury; Applied Spect., vol. 44, #7; 1990.

"Fiber–Optic Sampling Combined with an Imaging Spectrographed for Routine Raman Spectroscopy"; C.D. Newman, GG Pret & R.L. McCrury; Applied Spect. vol. 46, #2; 1992; pp. 262–265.

"Comparison of Multivariate Calibration Methods for Quantative Spectral Analysis"; E.V. Thomas et al.; Anal. Chem., vol. 62; pp. 1091–1099; May 15, 1990.

"Smoothing & Differentiation of Data by Simplified Least Squares Produses"; A. Savitzky et al.; Anal Chem., vol. 36, #8; Jul. 1964; pp. 1627–1639.

"NMR and Raman Spectroscopies Move from Lab to Plant"; M.D. Weiss; Today's Chemist at Work, Jan. 1995; pp. 25–28.

"Remote Near–IR Spectroscopy Over an Optical Fiber with a Modified FT Spectrometer"; D.D. Archibald, Applied Spect., vol. 42, #3; 1988; pp. 468–472.

Primary Examiner—Vincent P. McGraw
Attorney, Agent, or Firm—Richard C. Willson, Jr.; Richard D. Stone; A. J. Adamcik

[57] ABSTRACT

Benzene and substituted aromatic hydrocarbons can be predicted within ±0.31% vol or better, using Raman NIR spectroscopy and multivariate analysis, with optional fiberoptics multistreaming, preferably with Partial Least Squares regression analysis. The resulting signal can be used to control concentration of such compounds in product to desired levels.

66 Claims, 21 Drawing Sheets

HYDROCARBON ANALYSIS AND CONTROL BY RAMAN SPECTROSCOPY

Background of the Invention

I. Field of the Invention

The invention relates to the determination of the content of specified aromatic components in a variety of liquids, particularly the concentrations of various xylenes in hydrocarbon liquids.

Recent U.S. government environmental legislation has resulted in stringent regulatory agency guidelines for product makeup for the chemical and petroleum industries. The guidelines require tight control of the chemical composition of these industries' products, particularly the composition of gasoline. The benzene (and other aromatics, such as xylenes) content of gasoline has received particular attention, reformulated gasolines being limited, for example, to a maximum of one percent by volume of benzene. Because it is likely that governmental regulation of the chemical composition of various products and fuels will increase in the future, efficient chemical, refinery, and blending operations will require improved analytical procedures to insure compliance with the guidelines.

II. Description of the Prior Art

Prior patents related to the analysis of aromatics in hydrocarbon streams include U.S. Pat. No. 4,963,745 to Maggard, issued Oct. 16, 1990; U.S. Pat. No. 5,223,714 to Maggard, issued Jun. 29, 1993; U.S. Pat. No. 5,243,546 to Maggard, issued Sep. 7, 1993; U.S. Pat. No. 5,145,785 to Maggard and Welch, issued Sep. 8, 1992; international application WO 93/24823, published Dec. 9, 1993.

U.S. Pat. No. 5,349,188 to Maggard, issued Sep. 20, 1994, teaches the determination of octane generally, and U.S. Pat. No. 5,349,189 to Maggard, issued Sep. 20, 1994, teaches the determination of hydrocarbon groups by group type analysis.

Prior art teachings of the determination of individual hydrocarbon group types such as paraffins, isoparaffins, aromatics, naphthenes, and olefins (PIANO) can be found in prior literature and patents. A preferred technique is gas liquid chromatography, wherein a sample is injected into a partitioning column swept by an elutriating inert gas, e.g., helium, and the elapsed time for arrival at the end of the column is measured for each of the components, e.g., by a flame ionization detector, thermal conductivity, or other detector, as illustrated hereinafter in Example 17 and FIG. 17.

Conventionally, the percentages of each of the individual compounds detected by gas chromatography are grouped under their respective generic classifications in the PIANO classification system, and the relative percentage of each of the compounds (species) is determined in weight percent, volume percent, or mol percent as required. An example of this procedure is that taught by Analytical Automation Specialists, Inc. in their manual, "The Detailed Analysis of Petroleum Naphthas, Reformates, Gasoline and Condensates by High-Resolution Gas Chromatography", Operators Manual, P.O. Box 80653, Baton Rouge, La. 70898. Although precise, gas chromatography is time consuming and labor intensive, and the considerable lag time involved can result in unacceptable cost when productions errors occur.

Recently, near-infrared (NIR) spectrophotometric analysis has been used to perform structural group analysis of mixtures of saturated and aromatic hydrocarbons, and has been used in the quantitative analysis of benzene-toluene-paraffin mixtures by Leimer and Schmidt [Chem. Tech. (Leipzig), 25(2), 99–100]. Near infrared spectroscopy of hydrocarbon functional groups has also been described by Tosi and Pinto [Spectrochim Acta, Part A, 28, (3), 585–97]. U.S. Pat. No. 5,348,645 to Maggard et al describes NIR reflecto-absorbance spectroscopy to monitor octane and the concentration of total aromatics in petroleum fuels during the blending process.

None of the above mentioned references teach the analysis of individual species in the more complex mixtures routinely encountered in petroleum refineries. Such mixtures are often very complex; gasoline mixtures frequently contain over 300 compounds. Such mixtures almost always contain aromatics and olefins which are generally thought to have overlapping absorbance wavelengths in the mid-infrared region. This fact suggests that their overtones and combination bands in the near-infrared region would overlap even more, and thereby preclude determination of their individual concentrations in the mixtures. Further, individual molecular groups found (e.g. methylene) in naphthenes, are also found in paraffins and isoparaffins, as well as in substituted aromatic compounds and in olefins, so that the difficulty of analyzing for the concentration of individual molecular species is increased.

As far back as 1948, Raman spectroscopy was considered for determination of aromatics content in hydrocarbon mixtures (U.S. Pat. No. 2,527,121). For a variety of reasons, however, extensive use of this procedure as a quantitative technique has not occurred to the degree of mid-IR or near-IR absorbance/reflectance spectroscopic methods. One reason for this may be that a significant limitation of Raman spectroscopy has been the presence of interfering fluorescence signals (with the exception of aviation fuel) due to excitation by visible lasers.

Recently, FT-Raman spectrometers have been developed which eliminate the fluorescence problem in many cases by exciting in the NIR spectral region. This capability has sparked renewed interest in the use of Raman spectroscopy in the analysis of petroleum samples. For example, Shope, Vickers and Mann (Appl. Spectrosc., 1988, 42, 468) have demonstrated that when analytes are present in liquid mixtures as minor components, Raman spectroscopy is a viable quantitative technique. Using NIR-FT-Raman spectroscopy in combination with multivariate analysis techniques, Seasholtz, Archibald, Lorber and Kowalski (Appl. Spectrosc., 1989, 43, 1067) have demonstrated that quantitative analysis of percentage of fuel composition is possible for liquid fuel mixtures of unleaded gasoline, super-unleaded gasoline, and diesel fuels. In addition, Williams and co-workers (Anal. Chem., 1990, 62, 2553) have shown that NIR-FT-Raman spectroscopy in combination with multivariate statistics can be used to determine gas oil cetane number and cetane index. Chung, Clarke, and others have shown that Raman spectroscopy can be used in the quantitative analysis of aviation fuel in the determination of general hydrocarbon makeup, aromatic components, and additives (Appl. Spectrosc., 1991, 45, 1527; J. of Raman Spectrosc., 1991, 22, 79).

Recently, Allred and McCreery described an NIR dispersive Raman instrument utilizing a GaAlAs NIR diode laser, a single-stage imaging spectrograph, CCD detection, and a fiber-optic probe (Appl. Spectrosc., 1990, 44, 1229; Appl. Spectrosc., 1993, 46, 262) for benzene and $KNO_3$ analysis. More recently, Cooper and co-workers have demonstrated (Spectrochimica Acta, 1944, 50A, 567) that low-cost CCD detection is feasible for remote fiber-optic Raman detection.

While NIR technique is a viable analytical method for the majority of aromatic species, the spectral similarity of xylene isomers in the NIR absorbance region make quantitation of individual isomers difficult with NIR when more than one isomer is present in significant concentrations. Accordingly, there has remained a need for an effective procedure for measurement of substituted aromatics concentrations in a variety of liquids, particularly in fuels. The invention addresses this need.

SUMMARY OF THE INVENTION

Accordingly, the invention relates, in one embodiment, to a process for preparing an analytical model for analyzing specified liquid mixtures for the presence and concentrations of certain aromatic hydrocarbons. Broadly, in this process, multiple samples of liquid mixtures each comprising one or more of certain hydrocarbons in varying known or determined concentrations are irradiated with near infrared or other radiation, producing scattered Raman radiation emitted from each sample mixture. As used herein, the expressions "known concentration" or "known concentrations" indicate merely that the content of a particular mixture is known or defined, as, for example, by making up the mixture, or by appropriate analysis, which may be before or after the irradiation of the samples. The wavelengths present in the scattered light are characteristic of the molecules present, and the intensity of the scattered light is dependent on their concentrations. The Raman scattered radiation emitted from the respective samples is collected and then dispersed or transformed into spectra with intensities representing the chemical composition of the components of the mixtures of said samples and the concentrations of said components. Multivariate analysis or other mathematical manipulation is performed on some or all of the spectra, or mathematical functions thereof; e.g., to derive a regression model representative of mixtures containing one or more of the specified compositions. The resulting model is useful, as described more fully hereinafter, in analyzing a variety of liquid mixtures, particularly hydrocarbon liquids or mixtures, for the presence and concentrations of substituted aromatic hydrocarbons and/or benzene.

A variety of substituted aromatic hydrocarbons may be speciated, but the invention is particularly suited to the determining the presence and concentrations of alkyl, dialkyl, and alkenyl aromatic hydrocarbons containing from 7 to 20 carbon atoms, preferably those containing from 7 to 14 carbons. The model is especially useful for analyzing benzene-containing and xylene-containing mixtures, such as fuels or other streams containing benzene or one or more xylenes. Particularly preferred liquid mixtures for application of this procedure are hydrocarbon mixtures, such as petroleum liquids or mixtures, or synthetic petroleum mixtures. Fuels (gasoline), reformates, xylene-containing liquids or mixtures, solvents for aromatics, such as Sulfolane, and the like, may be analyzed, as described hereinafter. In one specific aspect of this embodiment, the multiple samples of liquid mixtures, each comprising or containing one or more substituted aromatics in varying predetermined concentrations, may be prepared as synthetic petroleum mixtures for the analysis. The respective samples of the mixtures are then, as described supra, radiated individually with near-infrared radiation, producing scattered Raman radiation emitted from each sample mixture, and are analyzed in the manner described.

In a second aspect of this embodiment, samples of substituted aromatic hydrocarbon- or benzene-containing liquid are recovered from a suitable source, such as a chemical plant stream or refinery stream. In a manner similar to that described previously, the respective samples of the mixtures are radiated individually with near-infrared radiation, producing scattered Raman radiation emitted from each sample mixture. Prior or subsequent to irradiation, at least a portion of the samples are analyzed by suitable conventional analysis, such as chromatographic analysis, to determine the nature and concentrations of the various components of interest in the samples. Based on the known concentrations and the spectra obtained, a model is produced, in the manner described previously, this model being based, to great advantage, on actual plant or refinery stream concentrations from the source or site chosen. As will be recognized by those skilled in the art, this procedure can produce an analytical model which eliminates having to perform conventional analysis more than once in the plant or refinery setting.

The use of the models produced, of course, is the great advantage of the invention. Accordingly, the invention, in another embodiment, relates to a process for determining the concentration of one or more substituted aromatics, or benzene, in a specified liquid sample, comprising irradiating the liquid sample with near infrared radiation, producing scattered Raman radiation emitted from said sample. The Raman scattered radiation emitted from the sample is collected, transferred, and dispersed or transformed into spectral intensities corresponding to the chemical composition of the components of the sample and concentration of said components. The concentrations of one or more substituted aromatics, etc., present are then determined by processing the spectral intensities from the sample according to the models previously mentioned, with the proviso or understanding that the source radiation wavelength in this embodiment is the same as or is correlated to that employed in establishing the models. As those skilled in the art will be aware, a sample may be static or dynamic, i.e., may vary over time. The terms "sample" or "samples", in this context, include flowing streams of such mixtures, which are particularly preferred for real-time control of processes in response to frequent analysis according to the invention. Temporal discrimination of a dynamic stream requires that spectra be acquired during a finite time interval. The shorter the interval, the higher temporal resolution of the changing concentration. Thus, spectra may be acquired over a very short time (seconds), or over a longer time (minutes), the term "spectra" herein encompassing also a single spectrum. Again, only selected portions of the spectra obtained need be processed, as will be evident to those skilled in the art; language hereinafter indicating processing of spectra is to be understood to indicate processing of all or of selected spectral regions. The speed of analysis obtainable by the present invention (less than one minute) enables on-line control response times not possible with past prior art chromatographic methods. The determination of different components may be made simultaneously and nearly continuously, providing on-line (or at-line) analysis without the need to return samples to control laboratories in refineries.

The invention thus provides, particularly with the use of modern fiber optics, a quick and efficient method of monitoring the concentration of a substituted aromatic hydrocarbon, such as xylene, or benzene, on line, and the monitoring system may be coupled, in the most preferred aspects of the invention, with a computer and other equipment to regulate the parameters of a process, e.g., to control the concentration of a particular component, e.g., benzene, in the liquids, such as hydrocarbon fuels, produced or to feed-forward the compositions of starting materials being fed to a process.

I. General Statement of the Invention

According to the invention, concentrations of substituted aromatics in various liquids, and benzene in hydrocarbon fuels, can be determined with great accuracy, e.g., ±0.31% vol or better, from a remote location using fiber-optic Raman spectroscopy with near-infrared diode laser excitation, utilizing multivariate regression analysis.

II. Utility of the Invention

This invention will find its greatest application in the petroleum refining industry, the techniques described being useful to monitor and control the amounts of individual substituted aromatic species in gasoline and middle distillate fuels and the benzene content of gasoline.

Another preferred application is the regulation of the allowable benzene content for reformulated fuel in gasoline blending systems using a blending program such as Ashland Petroleum's BOSS™ (Blend Optimization and Scheduling System), Chevron's GINO (Gasoline In-line Optimization), Oil Systems, Inc., MG Blend, or other similar blending optimization programs. Blending systems for use with the present invention, to provide blends having desired species analysis, can be of conventional design, usually involving the use of proportioning pumps or automatic control valves which control the addition rate for each of a series of components fed from different tanks or other sources. A preferred blending system comprises, for example, a system wherein a signal controls the feeding and blending of components having different benzene compositions into a common zone, whereby a product having a desired benzene composition is produced. A computer receiving the output signal from the spectrometer used to determine the concentration of a given component can readily process the information to not only provide the target species analysis in the finished blended hydrocarbon, e.g., gasoline, but also to provide the target blend at minimum cost, given the relative costs or species analysis enhancement values of the components being fed to the blending system.

Other applications of the invention include various catalytic processes, such as catalytic reforming, where a knowledge of feedstock composition and product composition is preferably used to determine reactor severity, e.g., the hydrogen uptake, temperature, pressure or unit space velocity in the reforming zone. Examples 4 and 5 herein respectively show fixed-bed and continuous, catalytic reformers monitored and controlled according to the invention to regulate the severity of the reforming (temperature, hydrogen pressure, hydrogen uptake, and/or unit space velocity) or moisture in the feed.

The invention is also suited to many applications of substituted aromatic hydrocarbon species analysis outside of the petroleum industry. An example is the monitoring of individual isomer concentration (e.g., ortho-xylene) during solvent purification in the chemical industry. Also, the invention can be used to monitor the purity and/or composition of various streams, the concentration changes which occur during a chemical reaction, and even impurity concentration of substituted aromatic hydrocarbon constituents.

Examples of preferred systems further include systems wherein the hydrocarbons being monitored are involved in a chemical reaction.

DETAILED DESCRIPTION OF THE INVENTION

Figure 1:
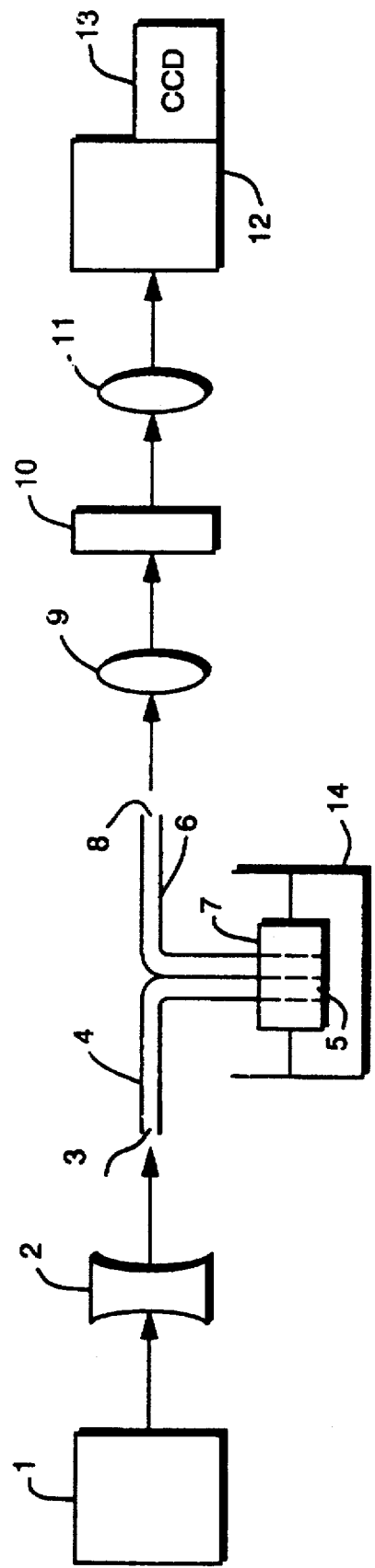
FIG. 1 of the drawing schematically illustrates a suitable Dispersive Raman apparatus, with fiber optic probe, for carrying out embodiments of the invention.

The source of radiation used to produce the Raman scattering will be varied according to the liquid treated. In the case of xylene-containing liquids (and other non-fluorescing liquids), the type of radiation source may be varied considerably, and a laser of suitable visible wavelength may be used. With petroleum liquids or other fluorescing samples, however, laser systems of near infrared wavelength are preferred. Despite the lower degree of fluorescence obtained by choosing a near-infrared laser, highly colored samples may still fluoresce and interfere with Raman shifts corresponding to the fingerprint region (i.e., about 1630–700 $cm^{-1}$). It is still possible to obtain Raman information in the C-H stretch region (i. e., about 3110–2560 $cm^{-1}$) using a Fourier Transform spectrometer; and speciation is still possible. In addition to the spectrometers specifically discussed hereinafter, other suitable dispersive and Fourier Transform spectrometers are available and may be used. The number of samples utilized for the model will vary with the application and desire for accuracy. For example, in the case of a synthetic fuel mixture, from 20 to 50 samples will be adequate, with more or less being used as desired or needed.

Table A lists preferred, more preferred and most preferred dispersive Raman spectral regions for determining the components according to the invention. Table B lists preferred, more preferred and most preferred FT-Raman spectral regions for determining specific components according to the invention.

TABLE A

HIGH CORRELATION DISPERSIVE RAMAN SPECTRAL REGIONS

| Component | Units | Preferred | More Preferred | Most Preferred |
|---|---|---|---|---|
| Metaxylene | $cm^{-1}$ | 1080–940, 810–680, 620–470 | 1060–940, 810–680 | 1080–940, 620–470 |
| Orthoxylene | $cm^{-1}$ | 1090–1020, 790–670, 630–550 | 1090–1020, 790–670 | 790–670, 630–550 |
| Paraxylene | $cm^{-1}$ | 1260–1120, 900–750, 520–420 | 1260–1120, 900–750 | 900–750, 520–420 |
| Benzene | $cm^{-1}$ | 1208–1166, 1012–956 | 1012–956 | 1208–1166 |
| Ethyl Benzene | $cm^{-1}$ | 1245–1194, 1059–970, 803–714 | 1059–970, 803–714 | 1245–1194, 1059–970 |
| Cumene | $cm^{-1}$ | 1240–1155, 1620–1494, 794–717, 1057–900 | 794–717, 1057–900 | 1240–1155, 1620–1494 |
| Styrene | $cm^{-1}$ | 1670–1600, 1500–1450, 1070–1050, 1010–960 | 1670–1600 | 1500–1450, 1070–1050, 1010–960 |
| Toluene | $cm^{-1}$ | 1245–1133, 1082–989, 849–760, 640–593, 570–505 | 1082–989, 849–760 | 1245–1133, 1082–989 |

TABLE B

HIGH CORRELATION FT-RAMAN SPECTRAL REGIONS

| Component | Units | Preferred | More Preferred | Most Preferred |
|---|---|---|---|---|
| Metaxylene | $cm^{-1}$ | 3600–2250, 1860–184 | 3600–2250 | 1860–184 |
| Orthoxylene | $cm^{-1}$ | 3600–2250, 1860–184 | 3600–2250 | 1860–184 |
| Paraxylene | $cm^{-1}$ | 3600–2250, 1860–184 | 3600–2250 | 1860–184 |
| Toluene | $cm^{-1}$ | 3600–2250, 1860–184 | 3600–2250 | 1860–184 |

TABLE B-continued

HIGH CORRELATION FT-RAMAN SPECTRAL REGIONS

| Component | Units | Preferred | More Preferred | Most Preferred |
|---|---|---|---|---|
| Benzene | $cm^{-1}$ | 3600–2250, 1860–184 | 3600–2250 | 1860–184 |
| Ethyl benzene | $cm^{-1}$ | 3600–2250, 1860–184 | 3600–2250 | 1860–184 |
| Cumene | $cm^{-1}$ | 3600–2250, 1860–184 | 3600–2250 | 1860–184 |
| Styrene | $cm^{-1}$ | 3600–2250, 1860–184 | 3600–2250 | 1860–184 |

Correlation of the spectra to the species concentrations of interest is accomplished using multivariate analysis. As utilized herein, the term "multivariate analysis" is understood to include all types of multivariate statistical analysis, with the procedures known as partial least squares (PLS), principal component regression (PCR), multiple linear regression (MLR) by classical or inverse least squares being preferred. By the PCR method, each spectrum in the calibration sample set is represented as an n-dimensional vector, where n is the number of points in the spectrum. Each vector (spectrum), is broken down into one or more components, plus an error vector to account for variation not explained by the factors. By this mathematical treatment or "decomposition," the autoscaled spectrum is represented as the weighted vector sum of the components plus the error vector. Each successive component accounts for the variation remaining in the calibration set, after subtracting the weighted contributions of all preceding components. The coefficients in the weighted sums (also known as "scores") are then correlated with the properties of interest (i.e., species concentrations) using multilinear regression. PLS is similar to PCR in that the spectra are decomposed into components ("latent variables"). However, by the PLS method, the spectra are weighted by the species concentrations prior to the decomposition step. The regression is accomplished during the decomposition, making a separate regression step unnecessary. There are two PLS methods in common use: PLS-1, which calculates a separate set of scores for each species concentration; and PLS-2, which, as does PCR, calculates a single set of scores for all species of interest. More detailed information on these methods can be found in the literature (Geladi, P. and B. R. Kowaiski, Partial Least-Squares Regression: A Tutorial, Anal. Chim. Acta 1986, 185, 1–17). Of the preprocessing options, autoscaling was found to give the best results upon cross-validation.

In the case of dispersive Raman spectroscopy, if a Fabry-Perot type diode laser is used for laser excitation, "mode hopping" may occur. This may be minimized by keeping the excitation laser, over the course of operations, in constant current mode while its temperature is stabilized. Mode hopping causes frequency shifts or line broadening in the Raman spectra. Since mode hopping of diode lasers is a function of both temperature and drive current, use of a diode laser in constant power mode often forces the drive current into regions of instability at given temperatures, thus inducing a mode hop. Since the spectra may be acquired over a one-minute integration period, the average change in laser intensity while in constant current mode over a total integration period is typically very small. Diode lasers with either internal or external gratings, e.g, distributed Bragg reflector diode lasers, are preferred over Fabry-Perot diode lasers since diode lasers with internal or external gratings eliminate mode hopping.

Outlier diagnostics (Thomas and Kaaland, Anal. Chem. 1990, 62, 1091) are used to generate leverage plots for the different spectra for each partial least squares regression analysis. The leverage of each spectral sample is indicative of how much of an effect each sample has on influencing the regression model. The leverage plots are useful for detecting artifacts (due to mode hopping, back-scattering of Raman modes from the excitation fiber into the collection fiber, cosmic rays or sampling errors).

Results from PLS or principal component analysis can be used directly or incorporated into a neural network to obtain the final model. Neural networks are discussed in several publications, including Long, J. R., V. G. Gregoriou, and P. J. Gemperline, Anal. Chem. 1990, 62, 1791–1797. Use of PCA and PLS scores as inputs to neural networks are discussed by Borggaard, C. and H. H. Thordberg (Anal. Chem. 1992, 64, 545–551).

As indicated, the procedures of the invention are applicable to any liquid mixture containing one or more substituted aromatic hydrocarbons and/or benzene. However, the invention is most adapted to use with petroleum mixtures, such as gasolines, aviation fuel, and diesel fuels. As used herein, the term "synthetic gasoline mixture" merely implies a prepared mixture of refinery components to cover the composition range in actual gasoline blends.

EXAMPLE 1

(Gasoline Properties by Dispersive Raman Spectroscopy)

In order to describe the invention more fully, reference is made to FIG. 1. The setup shown is analogous to that described in the aforementioned McCreery et al publication, which is hereby incorporated by reference. Accordingly, there is shown a radiation source 1, in this case a GaAlAs DBR diode laser (Spectra Diode Labs) which emits radiation in the near infrared. The radiation is filtered with dielectric band pass filter 2 (Janos) and is sent into the proximal end 3 of the excitation fiber 4 (200 micron quartz fiber optic, Polymicro). The probe tip 5 consists of the distal ends of the excitation fiber 4 and a parallel collection fiber 6, both fibers being sealed into a stainless steel tube 7 with epoxy and the ends polished. At the probe tip 5, the laser energy exits the excitation fiber 4 and the Raman scattered light thus produced is collected by the distal end of the parallel collection fiber optic 6. Light from the proximal end 8 of the collection fiber 6 is collimated with an f/2 plano-convex NIR reflection coated lens 9 and then filtered with a 850 nm holographic notch filter 10 (Kaiser Optical) to remove Rayleigh scattering before focusing the Raman signal with an f/4 lens 11 onto the slits (60 micron slit width) of an image corrected ¼ meter spectrograph 12 (Chromex). A 300 groove/mm grating blazed at 1 micron was used to disperse the Raman signal. A ST6UV charge coupled detector (CCD) 13 (Santa Barbara Instruments Group) thermoelectrically cooled to −35 C. was used to detect the dispersed signal. The detector 13 consists of 750 horizontal pixels (12 micron widths)×350 vertical pixels. The pixels are binned on chip by two in the horizontal direction and by 350 in the vertical direction giving a total of 375 superpixels. According to the invention, Raman spectra are acquired by placing the probe tip 5 directly into a sample which is provided in container or vessel 14 and integrating over 60 seconds. For a size perspective, the fiber-optic length for fiber 4 is 2 meters from the laser to the probe tip, and the length of fiber 6 is 3 meters from the probe tip to the spectrograph 12.

All spectra are recorded the same day over a four hour period during which the diode laser setting (805 nm) remains constant and the room temperature remains constant at 23° C. The incident power from laser 1 at the sample is ~50 mW, and the spectral resolution for the described system is ~10 cm$^{-1}$. Spectral processing and partial least squares regression analysis are performed using Pirouette multivariate software (Infometrix) or QuantIR (Nicolet).

In the case of probes which utilize lengthy fibers, e.g., several meters, a second dielectric band pass filter will be required near the distal end of excitation fiber 4. For example, approximately one-half meter from the distal end of excitation fiber 4, the fiber may be cleaved, and the laser beam may be collimated with a lens, directed through a band pass filter, and refocused with a second lens into the other cleaved lens of excitation fiber 4.

Table C is a statistical summary for Dispersive Raman calibrations for six species in synthetic gasoline mixtures. Listed for each calibration are number of calibration standards, number of PLS factors, Standard Error of Validation, Mean Error of Regression, and range of data for each component.

TABLE C

Summary of PLS Factors for Dispersive Fiber-optic Raman of 83 Ashland Petroleum Synthetic Gasoline Mixtures
Spectral Region: 1630–700 cm$^{-1}$

| Species | # of Standards | # of Factors | SEV[1] (% Vol) | Mean Error (Regression)[2] (% Vol) | Range of Data (% Vol) |
|---|---|---|---|---|---|
| Benzene | 83 | 11 | 0.093 | 0.0298 | 0.2–2.1 |
| Toluene | 83 | 7 | 0.505 | 0.2838 | 1.0–8.0 |
| Ethylbenzene | 83 | 11 | 0.200 | 0.0409 | 0.5–4.2 |
| ortho-Xylene | 83 | 5 | 0.248 | 0.1256 | 0.25–4.75 |
| meta-Xylene | 83 | 11 | 0.310 | 0.0778 | 1.5–9.1 |
| para-Xylene | 83 | 11 | 0.126 | 0.0312 | 0.6–3.6 |

[1]SEV is the square root of the sum of the squares of residuals divided by (n − k − 1), where n is the number of standards in the model and k is the number of factors in the model. Performed using "leave one out" tequnique.
[2]Mean Error (regression) is the sum of the absolute values of the difference between predicted and actual values, divided by n.

EXAMPLE 2

(Gasoline Properties by FT-Raman Spectroscopy)

Alternatively (FIG. 2), a FT-Raman (Fourier transform, near-infrared, Raman spectrometer) may be used, wherein the grating is replaced by a Michelson interferometer or other device capable of producing an interferogram from the Raman scattered light from the sample. By appropriate software, the Fourier transform of the interferogram is calculated to produce the spectrum. In the FT-Raman spectrometer, shown in 2a, the petroleum sample 4 in a glass container is placed in a holder in compartment 5. The sample is then irradiated with near infrared radiation (wavelength 1064 nm) from a Nd:YAG laser 1, using mirror 2, through an opening in parabolic collection mirror 3. Mirror 3 collects the scattered Raman and Rayleigh radiation at 180 degrees and collimates it for optimum collection efficiency. The collimated beam is sent to interferometer 6, filtered with a holographic notch filter 7 (to remove the Rayleigh scattered laser light) and finally detected by a high-purity, germanium detector 8. Alternatively, the FT-Raman spectrometer can be coupled to a fiber-optic probe for remote sampling. In this configuration (FIG. 2b), the laser beam from laser 1 is focused by lense 2 into the proximal end of excitation fiber 3. The distal end of excitation fiber 3 delivers the laser radiation to the remote sample 4. The Raman and Rayleigh scattered light is then collected by a collinear collection fiber 5 which delivers the radiation back to the spectrometer. The radiation exits the collection fiber 5 and is collimated by lens 6. As before, the collimated beam is sent to interferometer 7, filtered by holographic notch filter 8, and detected by detector 9.

In the case of probes which utilize lengthy fibers, e.g., several meters, a dielectric band pass filter will be required near the distal end of excitation fiber 3. For example, approximately one-half meter from the distal end of excitation fiber 3, the fiber may be cleaved, and the laser beam may be collimated with a lens, directed through a band pass filter, and refocused with a second lens into the other cleaved lens of excitation fiber 3.

Figure 2A:
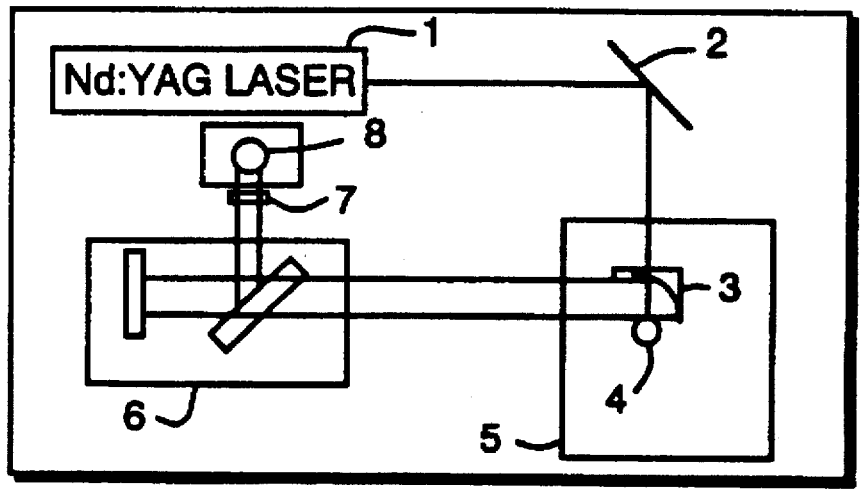
FIG. 2a schematically illustrates a suitable FT-Raman apparatus for carrying out embodiments of the invention.
Figure 2B:
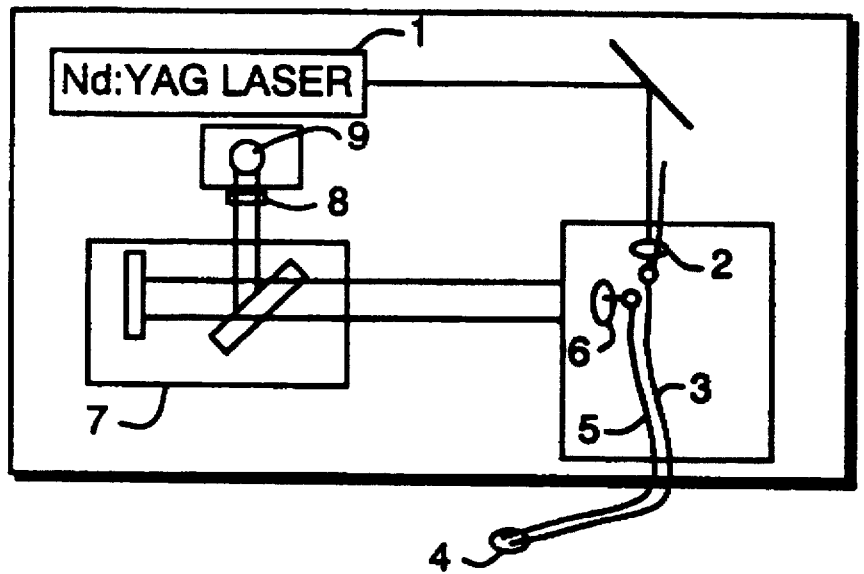
FIG. 2b schematically illustrates a suitable FT-Raman apparatus, equipped with a fiber optic probe, for carrying out embodiments of the invention.

The spectra of both configurations are substantially the same with the exception that the fiber-optic configuration results in a slightly lower intensity signal. Although FIGS. 1 and 2 illustrate the use of single fiber excitation and collection, those skilled in the art will appreciate that multiple fiber excitation and collection, with the optic fibers properly angled is preferred, such equipment being known.

Table D is a statistical summary for FT-Raman calibrations for six species in synthetic gasoline mixtures. Listed for each calibration are number of calibration standards, number of PLS factors, Standard Error of Validation, Mean Error of Regression, and range of data for each component.

TABLE D

Summary of PLS Factors for FT-Raman
of Ashland Petroleum Synthetic Gasoline Mixtures
Spectral Region: 3601.7–184.6 cm$^{-1}$

| Species | # of Standards | # of Factors | SEV (% Vol) | Mean Error (Regression) (% Vol) | Range of Data (% Vol) |
|---|---|---|---|---|---|
| Benzene | 169 | 10 | 0.157 | 0.0319 | 0.2–2.3 |
| Toluene | 168 | 7 | 0.491 | 0.2408 | 1.0–8.0 |
| Ethylbenzene | 170 | 11 | 0.130 | 0.0201 | 0.5–2.0 |
| ortho-Xylene | 170 | 8 | 0.106 | 0.0400 | 0.7–3.6 |
| meta-Xylene | 170 | 11 | 0.276 | 0.0402 | 1.4–4.9 |
| para-Xylene | 170 | 10 | 0.117 | 0.0223 | 0.6–2.1 |

[1]SEV is the square root of the sum of the squares of residuals divided by (n − k − 1), where n is the number of standards in the model and k is the number of factors in the model. Performed using "leave one out" tequnique.
[2]Mean Error (regression) is the sum of the absolute values of the difference between predicted and actual values, divided by n.

Description of the Preferred Embodiments

In each the following examples 3 through 16, a model is formulated, utilizing the sampling and multivariate analysis procedure described herein, for the liquid or liquids to be monitored. As will be appreciated by those skilled in the art, in the individual processes described, a radical change in liquid content, as for example, the substitution of a substantially different feedstock, e.g., substitution of oil shale liquid for Arabian light, would require derivation of a new model representing the ranges of variation of that feed.

EXAMPLE 3

(Invention Controlling a Fuel Blender)

Figure 3:
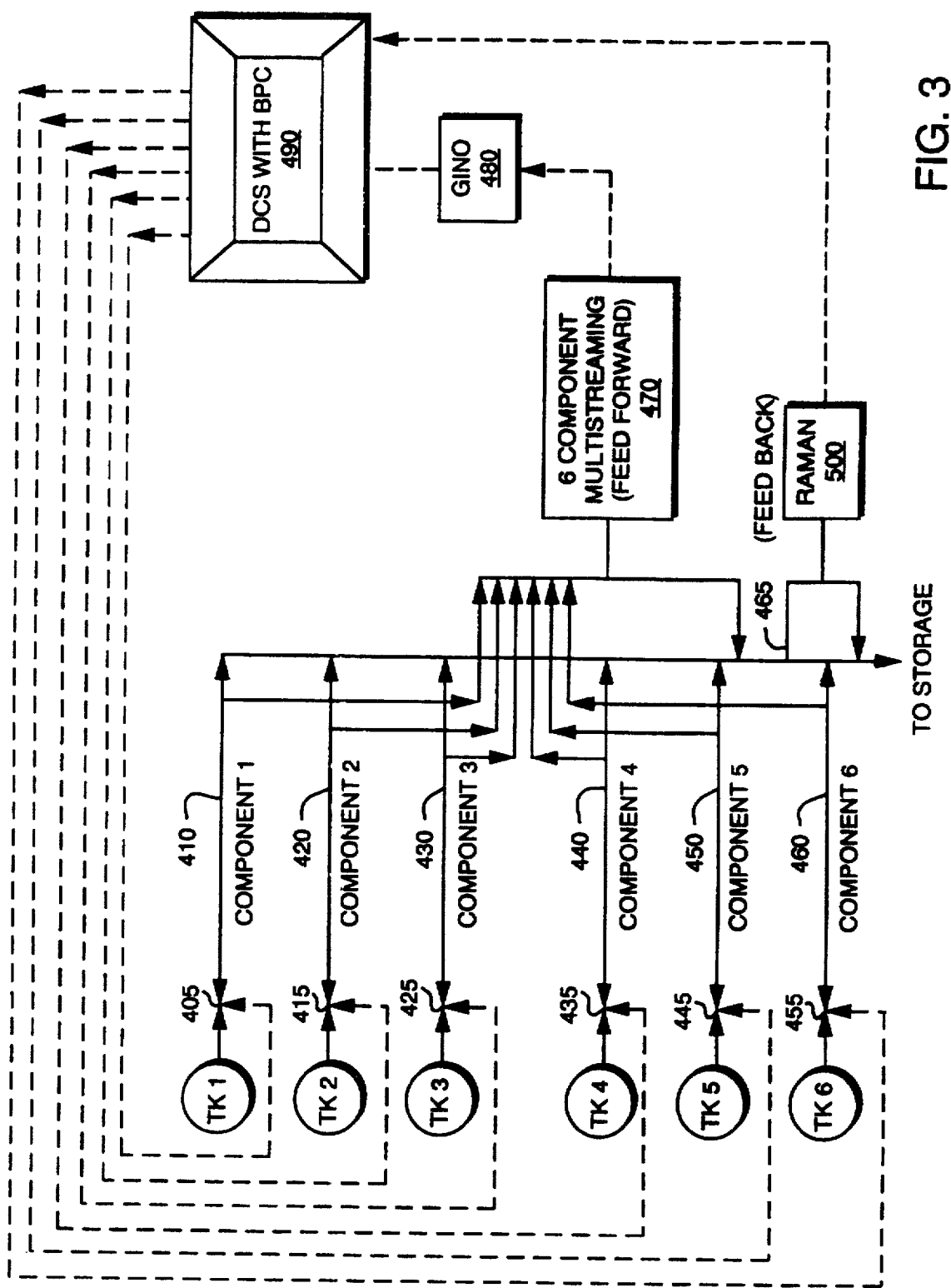
FIG. 3 illustrates schematically the fuel blending process described in Example 3.

FIG. 3 represents a control scheme for an on-line blender in a refinery, with both feed-forward and feedback, utilizing Raman spectra analysis of the invention to provide control.

In FIG. 3, the use of multistreaming, whereby the component streams are switched sequentially to a single probe, using valves, is illustrated. However, multiplexing, whereby a probe is located at each control point, or a combination of both, can also be used. In a multistreaming operation such as that illustrated in FIG. 3, component streams 410, 420, 430, 440, 450 and 460 are sequentially routed to the sample cell or sample in line probe of Raman spectrometer 470 which analyzes each stream for properties or components of interest, e.g., benzene. An output signal for each stream (proportional to vol % benzene) is then transmitted to optimizing software such as GINO. The GINO software, resident in blending computer 480, then continuously analyzes the signal, optimize and update the blend recipe in response thereto, and downloads the updated recipe to Blend Ratio Control (BRC) software which is resident in Distributed Control System (DCS) 490. The BRC software is capable of controlling DCS 490 which in turn may adjust the position of valves 405, 415, 425, 435, 445, and 455 to change the flow rates of component streams 410, 420, 430, 440, 450 and 460, respectively.

Another Raman spectrometer 500 can also be used in a feedback mode. That is, a slip stream 465 of the finished blend is directed to the sample probe or sample cell of Raman spectrometer 500, which analyzes the finished blend for benzene and other components of interest. DCS 490 then receives the feedback signal from Raman spectrometer 500 in the same manner as it receives the feed-forward signals from Raman spectrometer 470. The DCS 490 is configured to allow direct control of valves 405, 415, 425, 435, 445 and 455 by the feedback control loop to override the recipe established by the feed-forward control loop when necessary.

Raman spectrometer 500 may be the same instrument as Raman 470, with feed-forward and feedback functions operating in a multiplexing or multistreaming mode.

EXAMPLE 4

(Invention Controlling Fixed Bed Catalytic Reformer)

Figure 4:
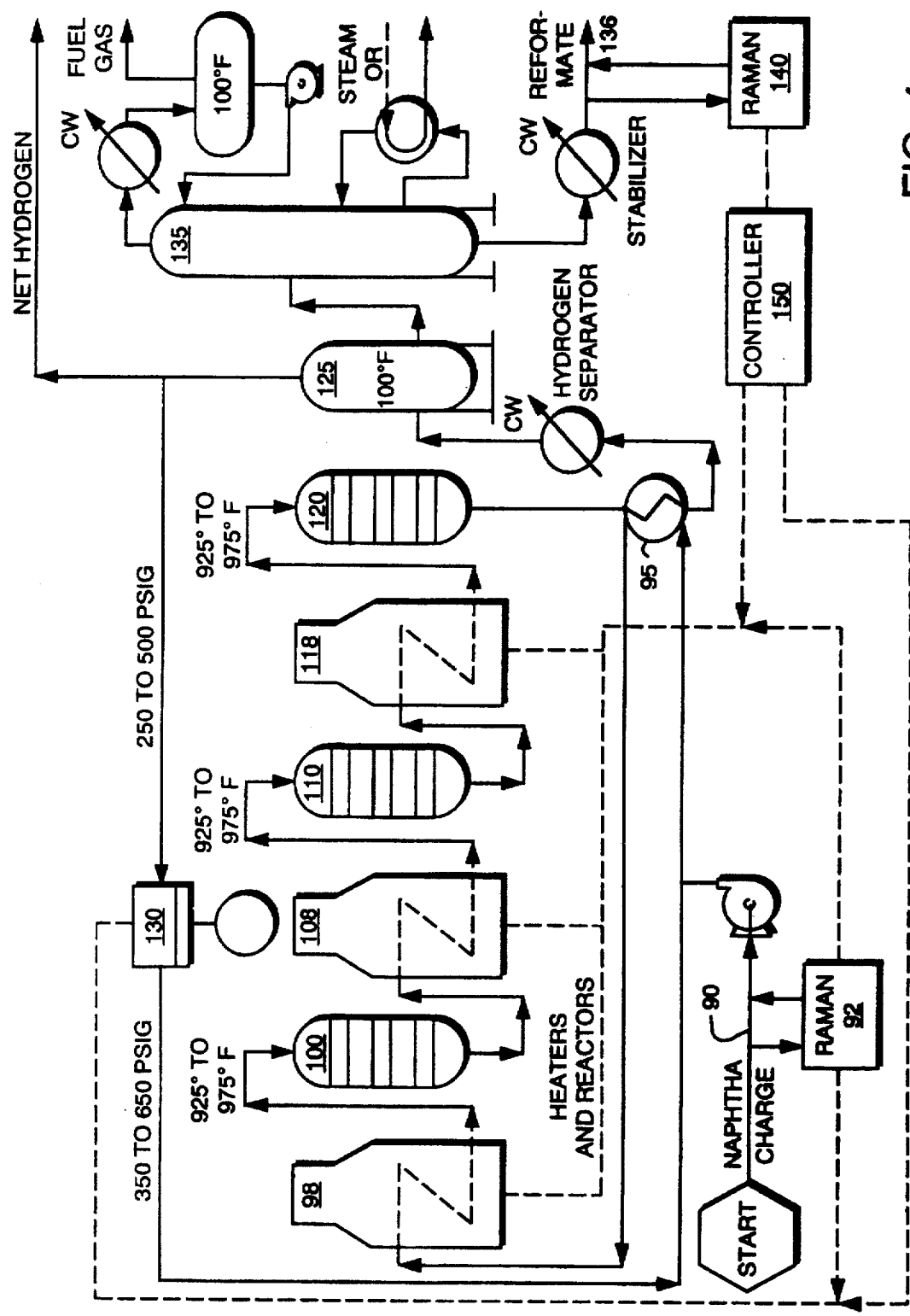
FIG. 4 illustrates schematically an embodiment in which a fixed-bed, catalytic reforming process, as described in Example 4, is controlled.

FIG. 4 shows schematically the process flow of a typical semi-regenerative catalytic reforming unit. Fixed-bed reforming units containing typical reforming catalysts are shown in series as 100, 110 and 120. The operation of the unit is generally as described in Gary and Handwerk, Petroleum Refining, under catalytic reforming and isomerization.

Referring to FIG. 4, naphtha charge in line 90 is pumped through economizing heat exchanger 95 and then into heater 98 where it is heated to the range of 496–524 C. (925–975 F.). The charge is then conducted to a first fixed bed reforming unit 100 which contains a conventional reforming catalyst of platinum. Products from reformer 100 move sequentially through heater 108, reformer 110, heater 118, and reformer 120. Product from reformer 120 moves on to hydrogen separator 125 and thence to fractionating column 135, the latter producing as bottoms a reformate stream 136 high in aromatics. Hydrogen recycle compressor 130 compresses hydrogen from hydrogen separator 125 and feeds hydrogen to mix with the naphtha charge 90 under varying pressures and throughputs of hydrogen. A Raman spectrometer 140 is placed on line in line 136 to determine the concentration of selected aromatic species, e.g., xylenes. As will be appreciated by those skilled in the art, the purpose of reforming is primarily to manufacture aromatic species. Accordingly, the lower the aromatics content analyzed by Raman spectrometer 140, the higher the temperature of heaters 98, 108 and 118 must be to increase the "severity" of the reforming process, and thereby to increase the aromatics in the product stream being measured by Raman spectrometer 140.

As indicated, according to the invention, a near-infrared (Raman) instrument 140 with closed-loop control capability and operating according to the techniques described above, is placed "on line" so that it analyzes a portion of the reformate product for aromatics. Noting any differences between the analyzed value and the preset desired value, the Raman closed-loop control unit 150 sends a signal to the heaters 98, 108, and 118 to increase or decrease their temperature or the temperature of any one of them. By increasing the temperature, the "severity" of the reforming process is increased, which tends to increase the aromatics and/or octane number of the finished reformate product being measured by the Raman unit 140. Alternatively, (or additionally) the signal from control unit 150 can be sent to the hydrogen recycle compressor 130 which increases the pressure of hydrogen in the feed, thus increasing the hydrogen uptake during the reforming process. This procedure serves to reduce the amount of aromatics in the reformate product.

Finally, Raman spectrometer 140 can be used to monitor catalyst performance as determined by product composition at a given severity.

Additionally, or alternatively, a different Raman spectrometer 92 (or the same Raman instrument 140 multiplexed for either multistreaming or multiplexing with fiber optics so as to analyze both the naphtha charge 90 and the reformate product), measures the naphtha charge and by "feed forward" predicts the temperature and hydrogen pressure which will be needed for heaters 98, 108 and 118, and hydrogen recycle compressor 130 in order to provide the desired product yield and level of aromatics in the reformate product being analyzed.

By the use of the invention, the aromatics species of the reformate can be controlled more closely than with similar methods employing gas chromatography because the Raman instruments 140 and/or 92 can analyze and respond in less than about one minute, providing close control and fast response. If a specific aromatic species such as benzene is especially desired to be increased or minimized in the reformate product, that specific species can be measured by the techniques described above, the measured value then compared with the preset desired value and the corresponding signal sent to the heaters and/or hydrogen compressor.

Similarly, space velocity can be increased in response to the Raman unit signal in order to reduce the severity of the reforming operation and reduce the aromatics in the produced reformate.

EXAMPLE 5

(Invention Controlling A Continuous Catalytic Reformer)

Figure 5:
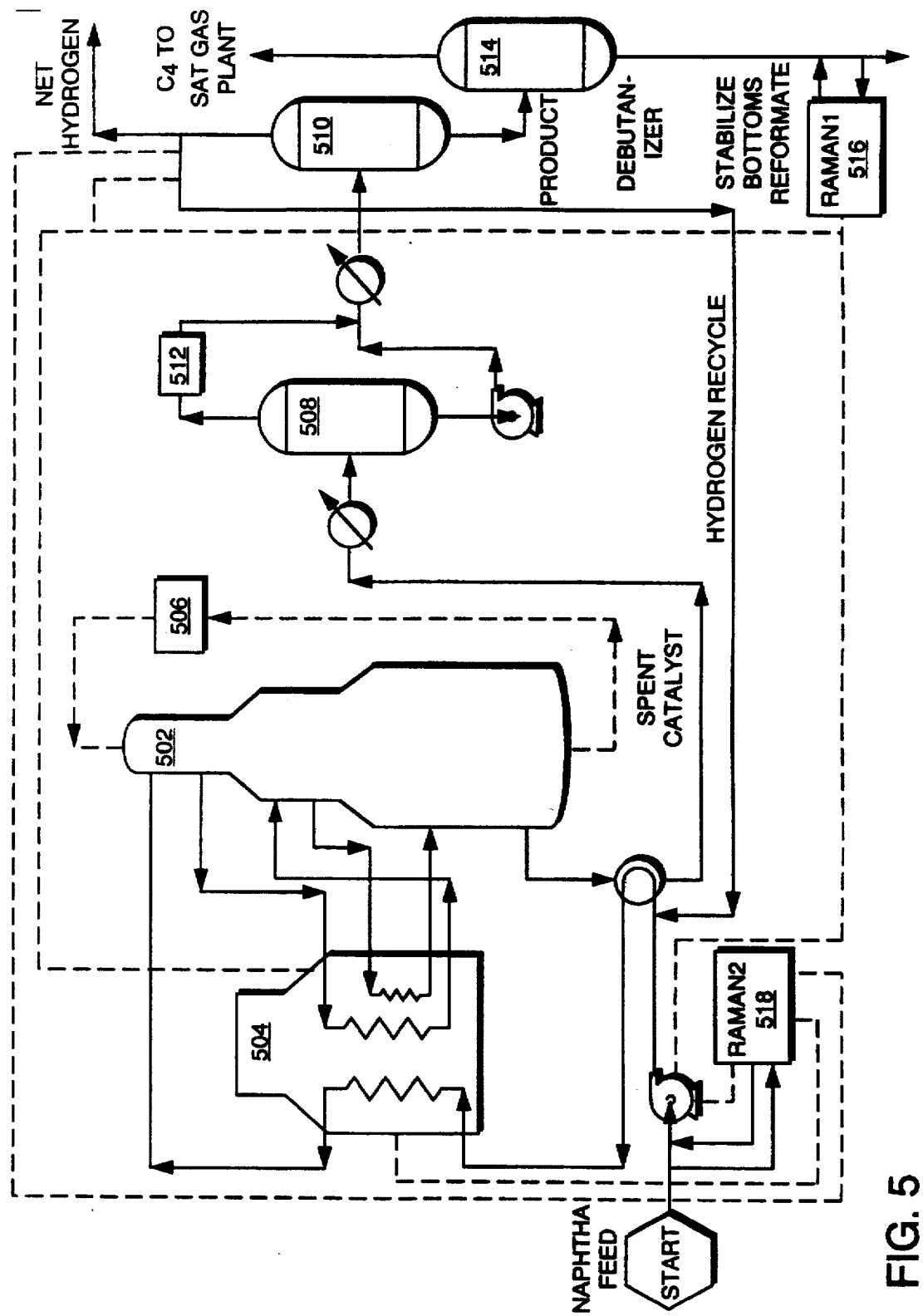
FIG. 5 illustrates schematically an embodiment in which a continuous catalytic reforming process, as described in Example 5, is controlled.

FIG. 5 is a diagram of a control system for a continuous catalytic reformer with both feed-forward and feedback Raman control.

A UOP-type continuous catalytic reformer (CCR) unit is controlled by the procedures of the present invention. In FIG. 5, 502 is the reactor, 504 is the heater, 506 is the catalytic regeneration section, 508 is the low pressure separator, 510 is the high pressure separator, 512 is the hydrogen compressor, and 514 is the debutanizer.

Naphtha feed is pumped through heater 504 and then to reactor 502 which contains recirculating catalyst. Regenerator 506 continuously regenerates the catalyst by burning off carbon, reducing and acidifying the catalyst, and then returning it to the top of reactor 502. The product is removed from reactor 502 to low-pressure separator 508 which removes hydrogen from the product. The removed hydrogen is compressed by hydrogen compressor 512. The product is then directed to high-pressure separator 510 which removes additional hydrogen, a portion of which is recombined with the naphtha feed. Product from high-pressure separator 510 is directed to debutanizer 514 which removes butane and lighter hydrocarbons. The bottom fraction from debutanizer 514 is sampled and analyzed by feedback analyzer RAMAN 1 516, which in turn is used in a feedback mode to control the feed rate, the temperature of heater 504 and the hydrogen recycle from high-pressure separator 510.

Feed-forward Raman Analyzer RAMAN2 518 is also used to sample the naphtha feed for control of the feed rate, the temperature of heater 504, and the hydrogen recycle from high-pressure separator 510. By use of feed-forward control in this configuration, the severity of the reforming process is adjusted based on the concentrations of aromatic forming species (such as naphthenes) in the feeds. In this way, aromatics such as benzene in the product is are controlled based on the chemical properties of the feedstocks. In addition, feed-forward Raman analyzer RAMAN2 518 alerts the operator to excessive amounts of undesirable species in the feed.

RAMAN 2 518 may be the same instrument as RAMAN 1 516 or a different Raman instrument, with feed-forward and feedback functions operating in a multiplexing or multistreaming mode. According to the invention, Raman analyzers RAMAN 1 516 and RAMAN2 518 sample the feed and the stabilizer bottoms.

EXAMPLE 6

(The invention controlling the Alkymax Process)

Figure 6:
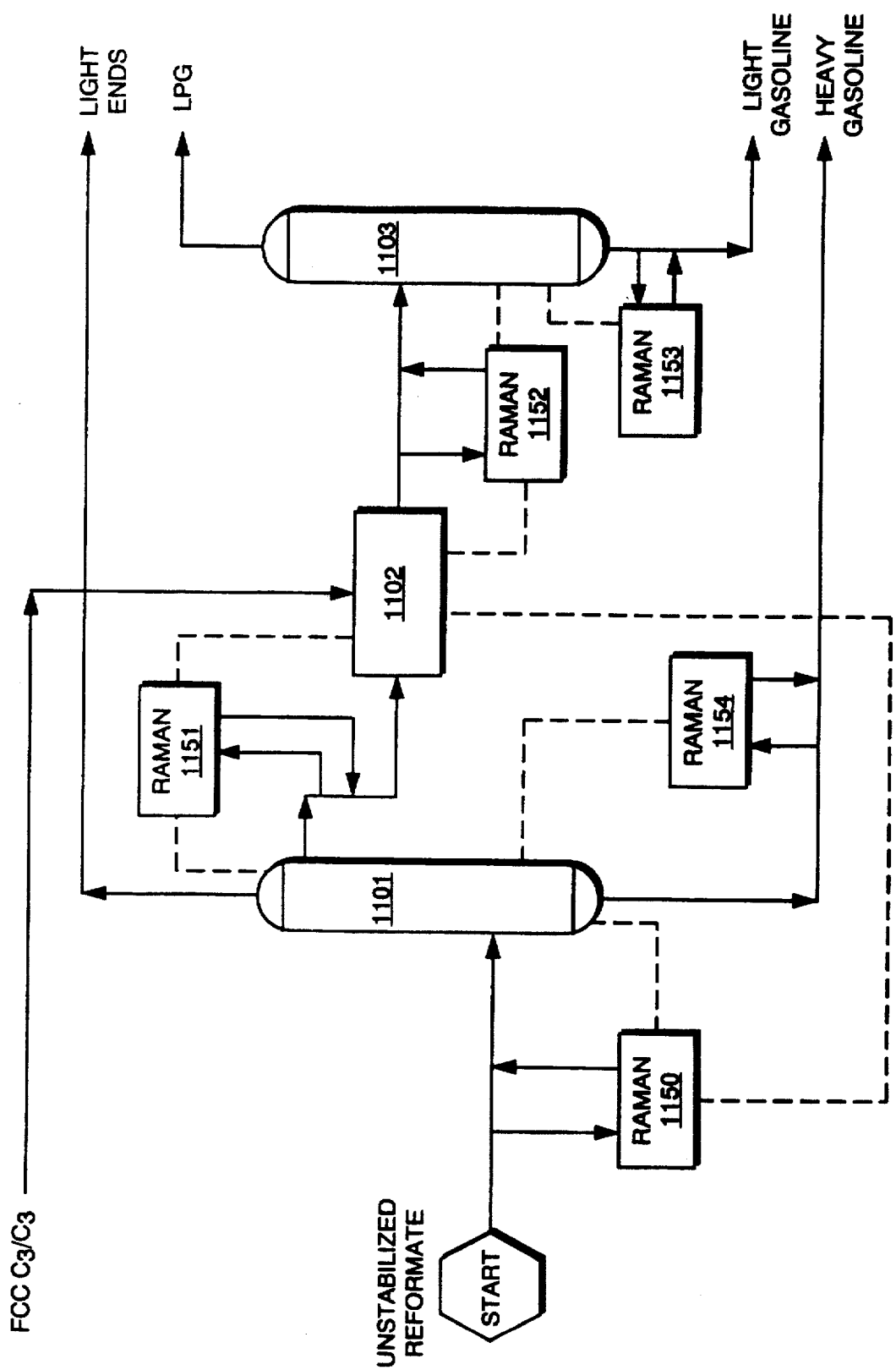
FIG. 6 illustrates schematically an embodiment in which the Alkymax® process of Example 6 is controlled.

Referring to FIG. 6, the Alkymax process uses a fixed catalyst bed to alkylate benzene in stabilized or unstabilized reformate, with light olefins (C2–C4). The operation of the unit is generally as described in Hydrocarbon Processing Refining Handbook, November, 1990, p. 138. The objective is to reduce benzene in the gasoline pool. This allows more flexibility in reformulated gasoline production. Splitter 1101 separates unstabilized reformate into a heavy gasoline (bottoms) and a light overhead fraction. There is a fraction drawn from the side which contains most of the benzene. This stream is combined with an olefin stream, typically from a catalytic cracker. The combined stream is passed through reactor vessel 1102 which contains the catalyst. Effluent from reactor 1102 is fractionated in stabilizer 1103 to produce LPG as overhead and a light gasoline product in the bottoms. Raman spectrometers 1150 and 1151 are used (respectively) for feed-forward and feedback control of the fractionation conditions in Splitter 1101, in order to optimize the isolation of benzene in the benzene sidecut. Both Raman spectrometer 1150 and 1151 may also be used for feed-forward control of Reactor 1102, based on the analyzed composition (e.g., benzene, toluene or xylenes) of the feedstock and the benzene sidecut, respectively. Raman spectrometer 1152 may be used either for feedback control of Reactor 1102, for feed-forward control of stabilizer 1103, or both in a multistreaming or multiplexed mode. Raman spectrometer 1154 and Raman spectrometer 1153 can be used for feedback control of Splitter 1101 and Stabilizer 1103, respectively. Raman spectrometers 1150–1154 may be separate instruments. Alternatively, some or all of them may be combined as a single instrument operating in a multistreaming or a multiplexed mode.

EXAMPLE 7

(The invention controlling a sulfolane or similar aromatic extraction unit)

Figure 7A:
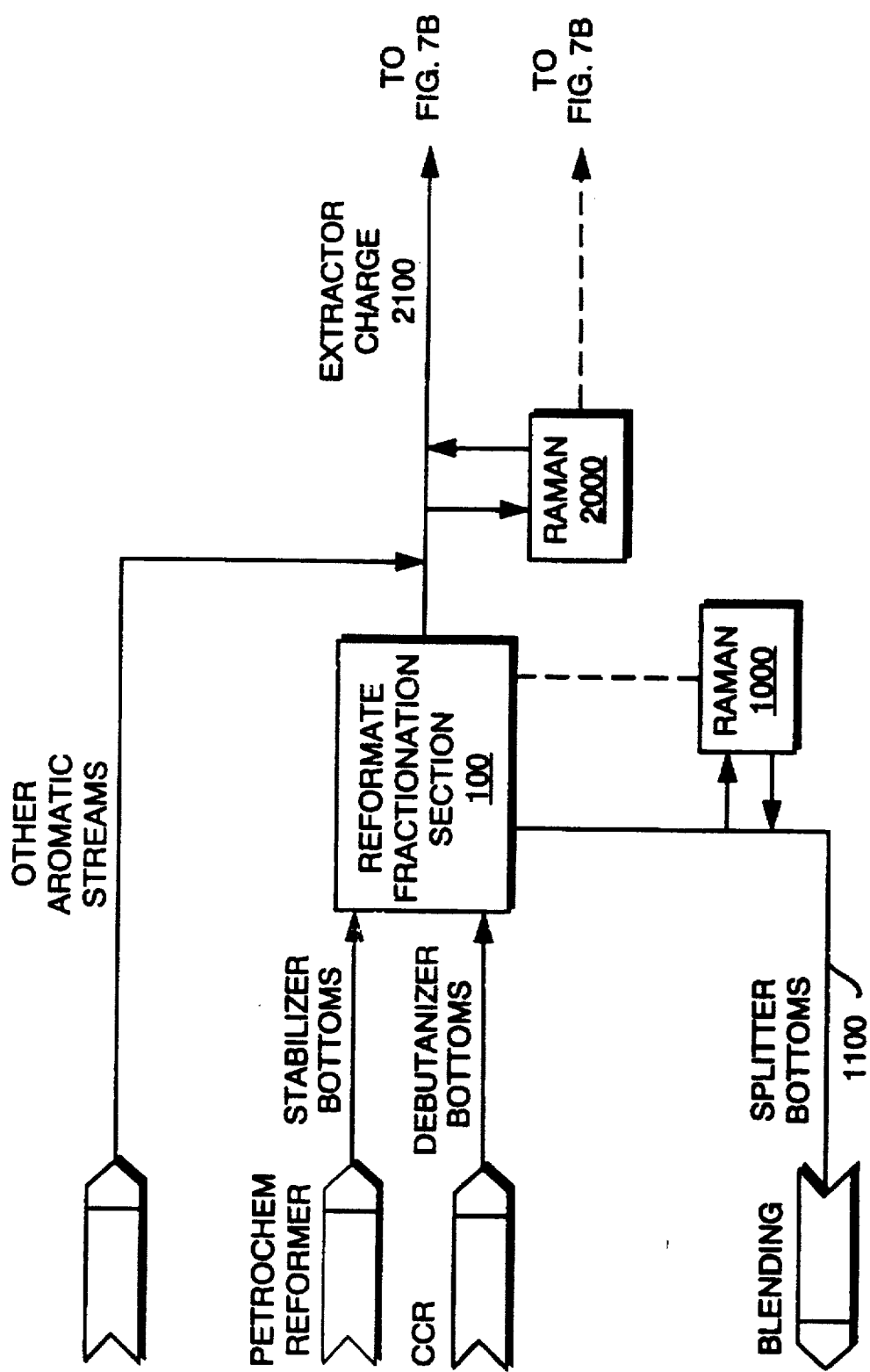
FIG. 7 illustrates schematically an embodiment in which the sulfolane or similar aromatic extraction unit of Example 7 is controlled.
Figure 7B:
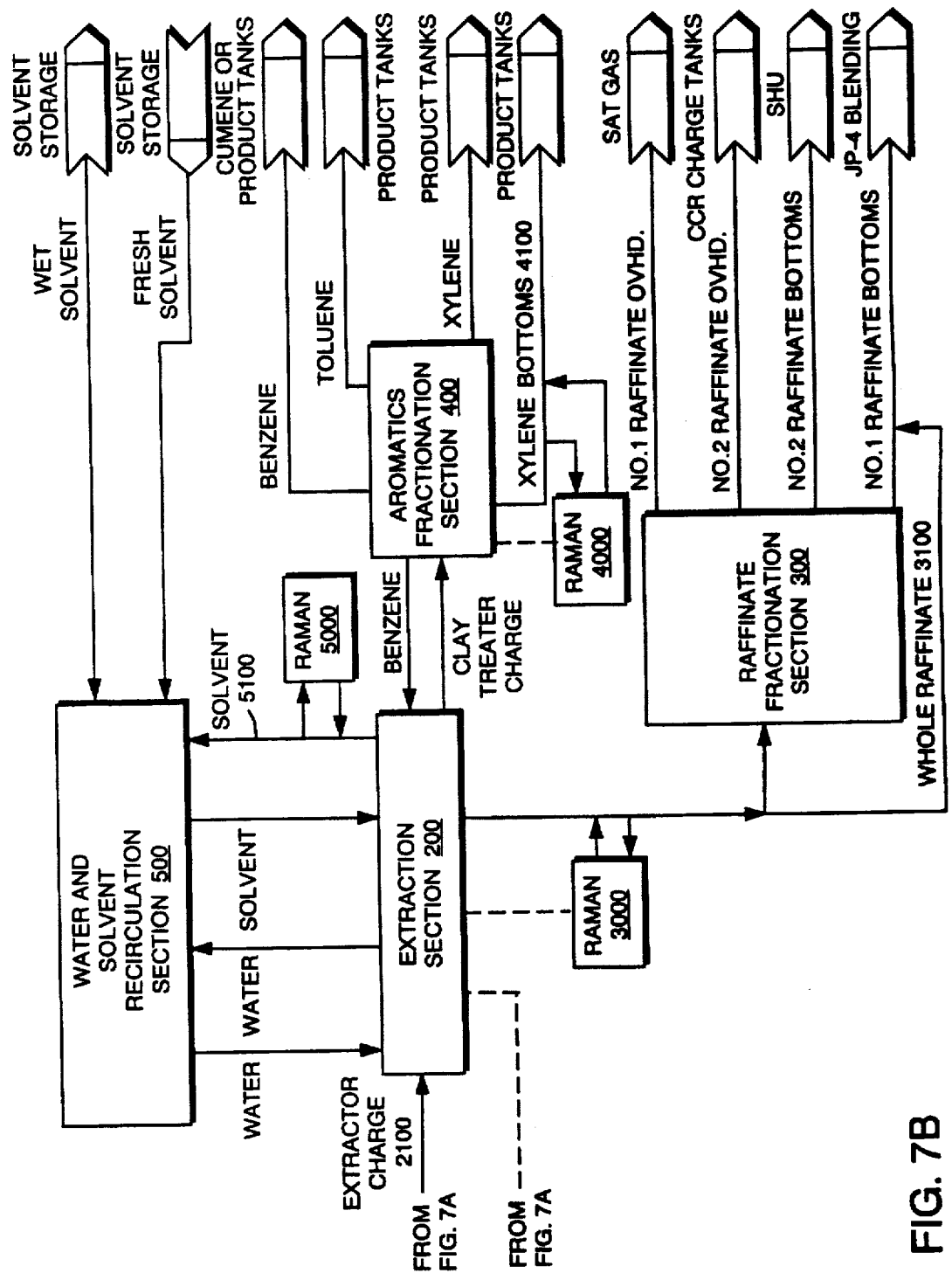

Referring to FIG. 7, the Sulfolane aromatics extraction unit is named for the chemical name of the extraction solvent ($C_4H_8SO_2$). Reformate feeds and other benzene, toluene and xylene (BTX) streams are mixed and then fractionated in Reformate Fractionation Section 100. This section consists of two towers in series. The first tower (dehexanizer) removes light material. The dehexanized bottoms are then fed to the second tower which takes a heart cut (consisting of benzene through xylene range material) as overhead, for use as Extractor Charge 2100 to Extraction Section 200. The bottoms fraction from the second tower (Splitter Bottoms 1100) is used for gasoline blending.

In Extraction Section 200, Extractor Charge 2100 is mixed with enriched aromatic streams from other units. These enriched aromatic streams may also include such feedstocks as BTX fractions from desulfurized coal tar light oil. The combined stream is extracted using Sulfolane solvent. Most of the extracted aromatics are recovered from the enriched solvent by a stripper followed by a recovery column. Residual quantities of aromatics are further removed from the solvent by a solvent regenerator located in Water/Solvent Recirculation Section 500. Most of the non-aromatics remain in the raffinate.

Whole Raffinate 3100 is water washed and then fractionated in Raffinate Fractionation Section 300. This section consists of two towers and produces various streams for jet fuel blending and for charge to other units.

In Aromatics Fractionation section 400, the extract is treated with clay to remove trace amounts of olefins, then fractionated in a series of four towers to produce benzene, toluene, xylene, and xylene bottoms product in line 4100. Some benzene and light paraffins from the first tower overhead are returned to the extractor as reflux. Overhead products from the four towers are quite pure: Benzene and toluene products are over 99.9% pure. Xylene product is 98.8% pure. The xylene bottoms (from the fourth tower) contain some xylene and longer chain (C7 and C8) aliphatics.

Water and Solvent Recirculation Section 500 recovers solvent from the raffinate wash water and recycles both liquids. This section contains the solvent regenerator to remove residual BTX from lean solvent stream 5100.

Raman spectrometer 1000, 2000, 3000, 4000 and 5000 are placed at-line on streams 1100, 2100, 3100, 4100 and 5100. Benzene content in heavy reformate stream 1100 can be predicted by on-line Raman spectrometer 1000 and is useful for feed-forward control and optimization of reformulated gasoline blending. Raman BTX measurements at this point can also be used in a feedback mode to control temperatures, reflux ratios and other conditions of the two distillation towers in Reformate Fractionation Section 100.

Similarly, on-line measurements of BTX in extractor charge 2100 by Raman spectrometer 2000, can be used in a feed-forward mode to control extraction conditions in Extraction Section 200, particularly the ratio of solvent to feed ("treat ratio").

Raffinate stream 3100 can contain some aromatics, but it is desirable to keep xylene content below 0.5%. It is important to control BTX in whole raffinate stream 3100 as well as in the bottom fraction from the first tower because of the use of these streams for jet fuel blending. Excessive aromatics in jet fuel leads to thermal cracking and fouling of fuel lines. Control of this quantity is provided by Raman spectrometer 3000 in a feedback control mode to Extraction section 200, as well as the above-mentioned feedforward control of this section by Raman 2000.

On-line Raman spectrometer 4000 is used for feedback control of xylenes in Xylene Bottoms stream 4100. Using such feedback control, temperatures and reflux conditions can be optimized in each of the four towers in Aromatics Fractionation Section 400.

On-line measurements of BTX in Solvent Regenerator Feed 5100, are a measure of the efficiency of BTX recovery from the enriched solvent.

Raman spectrometers 1000, 2000, 3000, 4000 and 5000 may be separate instruments. Alternatively, some or all of them may be combined as a single instrument operating in a multistreaming or a multiplexed mode.

EXAMPLE 8

(The invention controlling a toluene disproportionation process)

Figure 8:
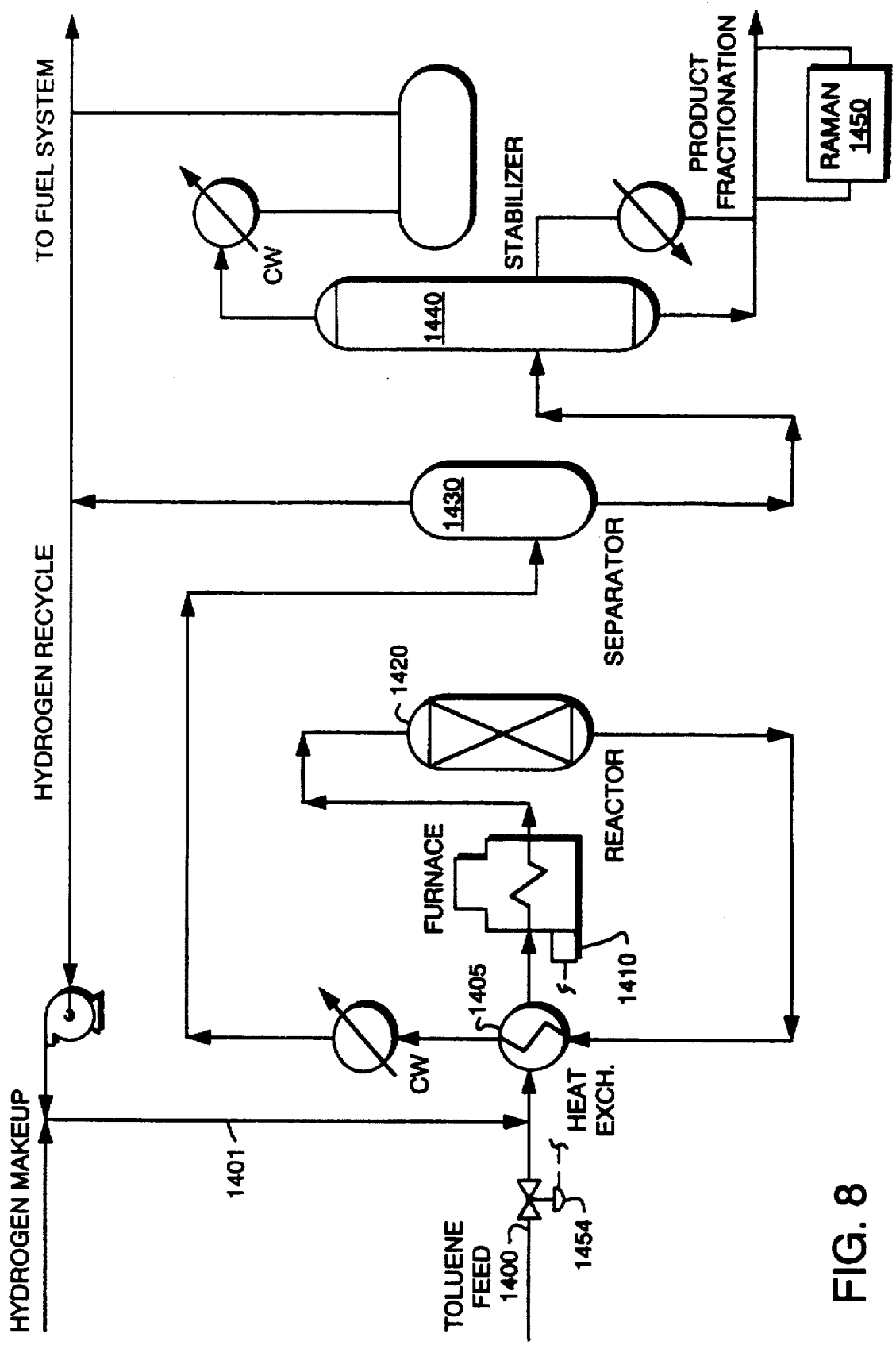
FIG. 8 illustrates schematically an embodiment in which the toluene disproportionation process of Example 8 is controlled.

Referring to FIG. 8, the Mobil Selective Toluene Disproportionation Process (MSTDP) converts toluene to high-purity benzene and a xylene product with an unusually high percentage of para-xylene. The operation of the unit is generally as described in Hydrocarbon Processing Petrochemical Handbook, March, 1993, p. 166. Dry toluene feedstock in line 1400 is combined with a hydrogen-rich gas obtained from recycle with makeup hydrogen added. The combined stream is heated by Heat Exchanger 1405 and Furnace 1410 and then charged to Reactor 1420, where the toluene (in the vapor phase) disproportionates into benzene and para-xylene (90% selectivity), by aid of a proprietary catalyst. The reactor effluent passes through Heat Exchanger 1405 to Separator 1430, which separates recycle hydrogen from the product. Light ends are separated in Stabilizer 1440. The remaining bottoms are fractionated and unreacted toluene recycled to extinction. Raman spectrometer 1450 is used to monitor and control the composition of the product mixture, which typically consists of about 15% benzene, 70% toluene, 14% xylenes (90% of which is para-xylene), and 1% ethylbenzene plus C9+ aromatics.

EXAMPLE 9

(The invention controlling a light paraffin aromatization)

Figure 9:
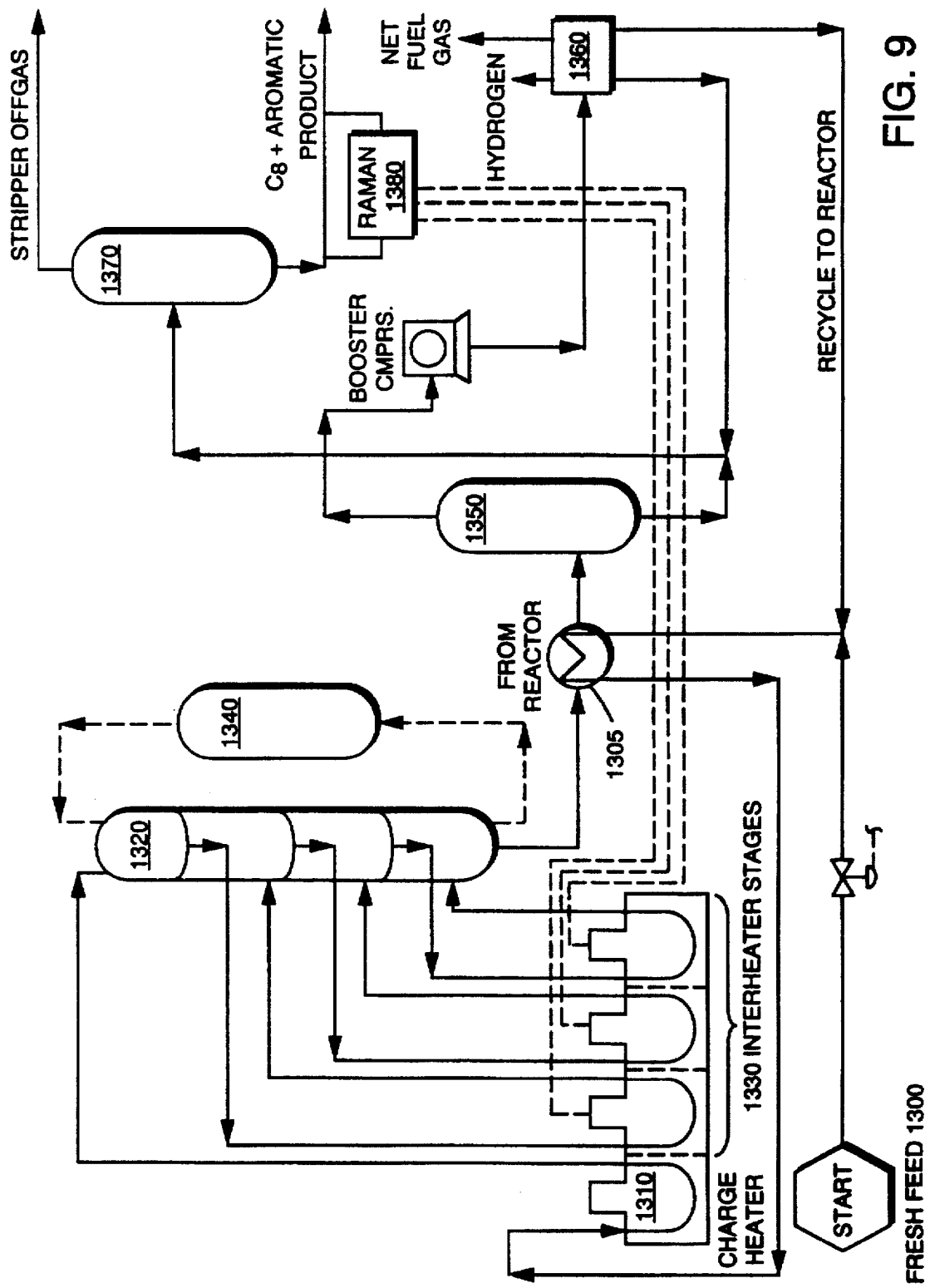
FIG. 9 illustrates schematically an embodiment in which the Light Paraffin Aromatization process of Example 9 is controlled.

It is possible to convert LPG feedstocks to aromatics using a reforming process as illustrated in FIG. 9. The operation of the unit is generally as described in Hydrocarbon Processing Petrochemical Handbook, March, 1993, p. 168. Fresh feed 1300, consisting of propane and butanes, is combined with recycle LPG, passed through Heat Exchanger 1305, and is heated in charge heater 1310. The heated feed is then charged to a series of stacked, radial-flow reactors 1320. Catalyst is regenerated in Regenerator 1340. Interheater stages 1330 serve to counteract the cooling from endothermic reforming reactions; and temperature in each reactor stage is thereby adjusted in order to maximize conversion and selectivity. Reactor products are directed to Separator 1350 via Heat Exchanger 1305. Overhead vapors from Separator 1350 are compressed and sent to Gas Recovery Section 1360, which separates the compressed vapors into three streams: hydrogen, fuel gas and recycle LPG. The liquid bottom stream from Separator 1350 is then sent to Stripper 1370, which separates light saturates from the aromatic products. The aromatic product stream typically contains about 27% benzene, 43% toluene, 22% $C_8$ aromatics and 8% $C_{8+}$ aromatics. Raman spectrometer 1380 is used to monitor the product composition and used in a feedback mode to control the temperatures of interheater stages 1330.

EXAMPLE 10

(The invention controlling a cumene production process)

In a process using an aluminum chloride-hydrogen chloride catalyst 1654, benzene 1658 is alkylated with propylene

17

Figure 10:
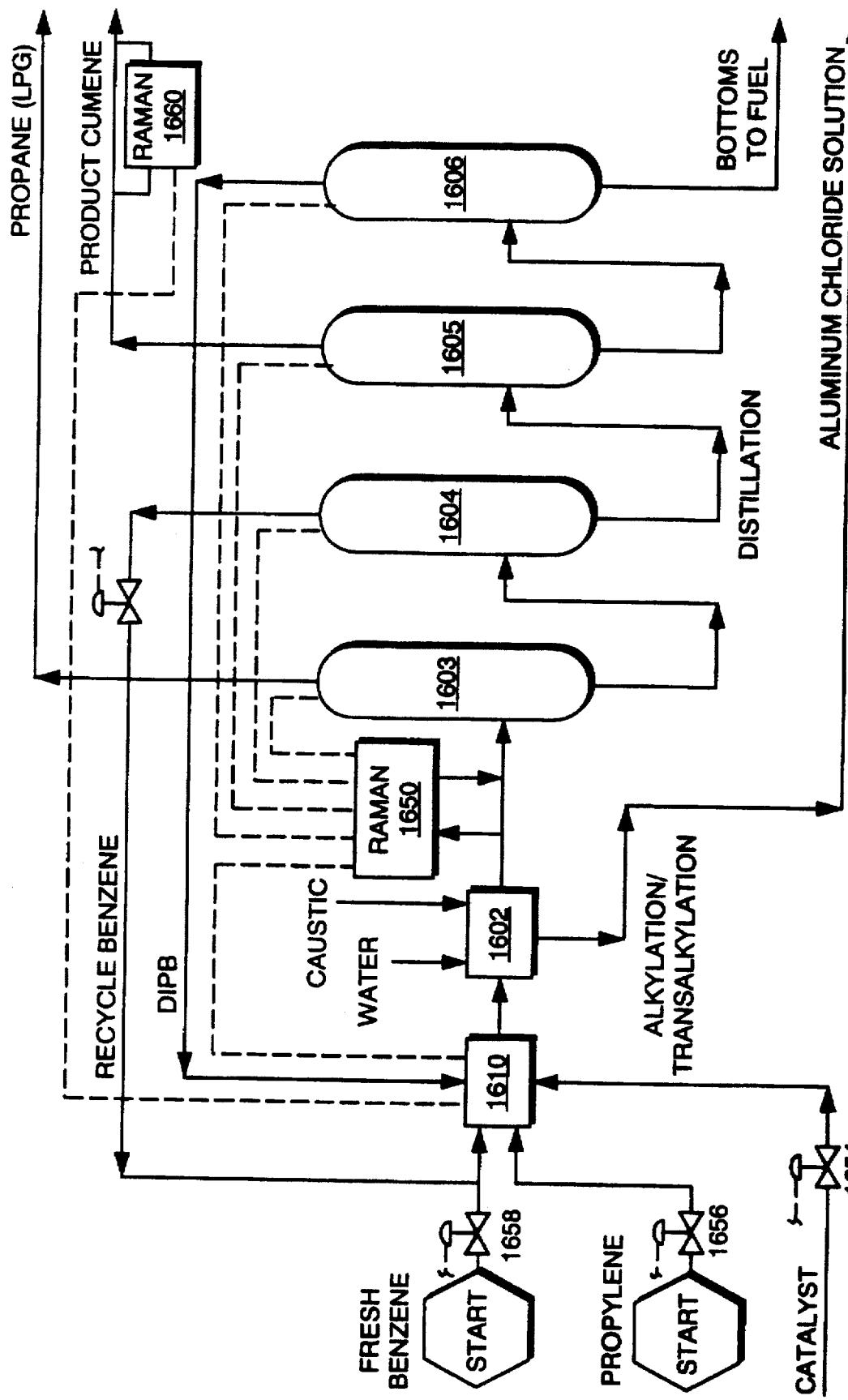
FIG. 10 illustrates schematically an embodiment in which the cumene production process of Example 10 is controlled.

1656 to yield cumene in high yields. The operation of the unit is illustrated in FIG. 10 and is generally as described in *Hydrocarbon Processing Petrochemical Handbook*, March, 1993, p. 175. The two feedstock materials are mixed in Reactor 1610 with catalyst and recycle benzene and propylene. The reaction takes place under mild conditions. Multiple alkylation takes place to form diisopropyl benzene and other polyalkyl benzenes, but these products can be recycled to a transalkylation zone in Reactor 1610 to form more cumene. Catalyst is removed from the reactor effluent with water and caustic in Washer 1602. The overhead fractions are then taken from the washed effluent in a series of columns: column 1603 to separate propane (LPG), column 1604 to separate unreacted benzene, column 1605 to separate product cumene, and column 1606 to separate diisopropyl benzene from the remaining heavy bottoms fraction. Benzene and diisopropyl benzene are both recycled to Reactor 1610. Raman spectrometer 1650 is used for feed-forward control of the temperatures and other conditions in columns 1603, 1604, 1605 and 1606, so that fractionation of the reactor effluent is optimized, e.g., to minimize concentration of diisopropyl benzene in the product cumene. Feedback control of the transalkylation zone of Reactor 16 10 is also possible using Raman measurements of diisopropyl benzene at this point. Alternatively or additionally, Raman spectrometer 1660 which monitors the product cumene, can be used for feedback control of columns 1603–1606.

Raman spectrometers 1650 and 1660 may be separate instruments. Alternatively, they may be combined as a single instrument operating in a multistreaming or a multiplexed mode.

EXAMPLE 11

(The invention controlling a process for making cyclohexane from benzene)

Figure 11:
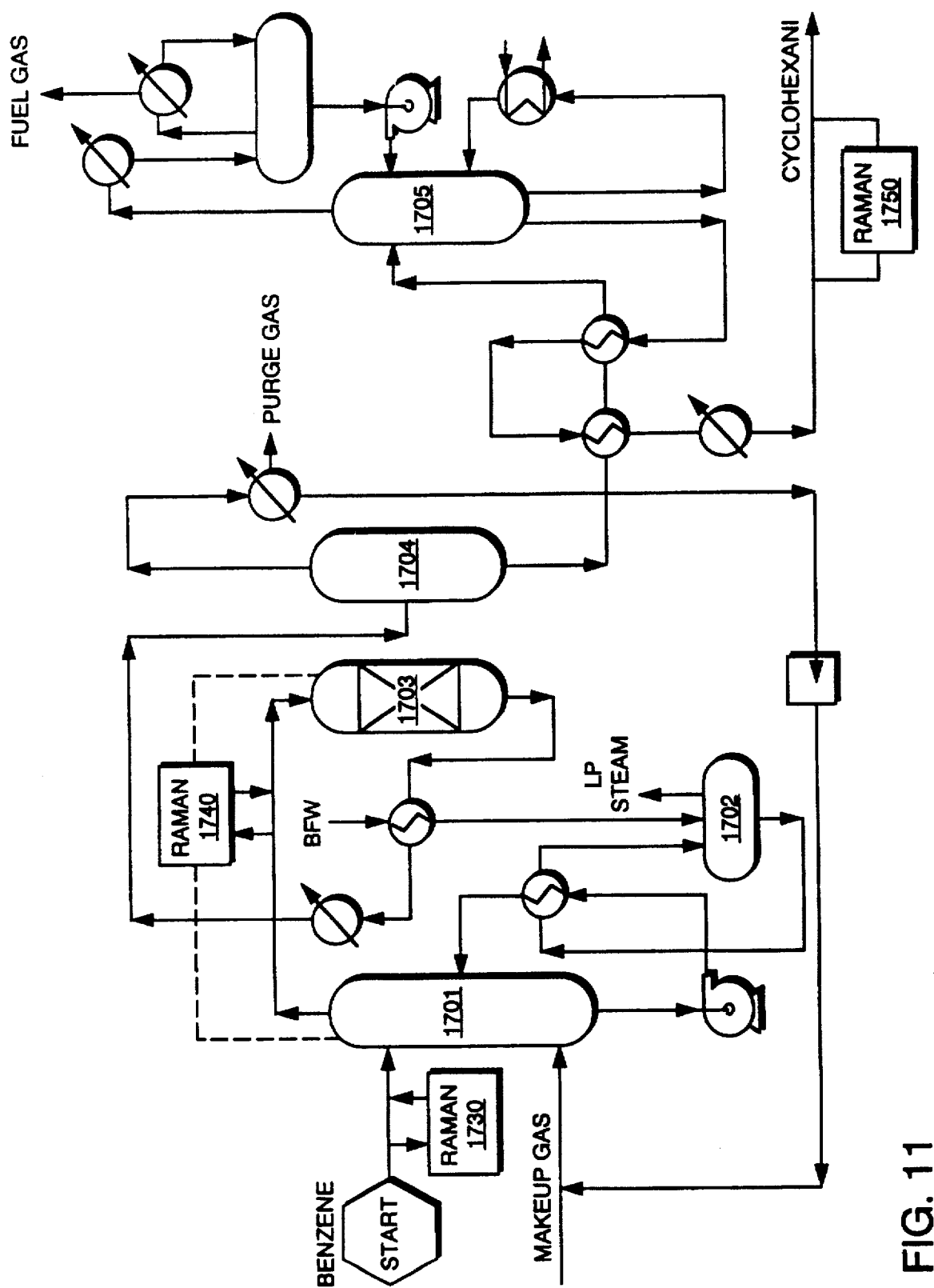
FIG. 11 illustrates schematically an embodiment in which a process for making cyclohexane from benzene, as described in Example 11, is controlled.

This process is illustrated in FIG. 11 and can be performed generally as described in *Hydrocarbon Processing Petrochemical Handbook*, March, 1993, p. 176. Catalytic hydrogenation of benzene to cyclohexane is accomplished by the following process: Feedstock benzene is combined with hydrogen-rich recycle gas and makeup hydrogen in Reactor 1701. To keep the catalyst suspended, the reactants are kept in constant circulation through Reactor 1701 using a pump-around arrangement equipped with Heat Exchanger 1702 to dissipate heat from the exothermic reaction and generate low-pressure steam. Effluent from Reactor 1701 passes through a small secondary reactor 1703 to complete the reaction if catalyst activity in the main reactor decreases or the conversion drops below specifications for some other reason. The effluent from Secondary Reactor 1703 passes through another heat exchanger and is fed to High-Pressure Separator 1704 to remove recycle gas as overhead. Hydrogen and other light, dissolved gases are removed from the bottom fraction in Stabilizer 1705, and the remaining product cyclohexane is cooled. The purity of the product depends largely on the purity of the feed benzene. Raman spectrometer 1730 is used to monitor the purity of the feed benzene as an indication of the purity to be expected in the product cyclohexane which itself is monitored by Raman spectrometer 1750. Benzene measurement by Raman spectrometer 1740 provides a measure of the extent of hydrogenation by Main Reactor 1701 and is used for feedback control of Main Reactor 1701 and/or feed-forward control of Secondary Reactor 1703.

Raman spectrometers 1730, 1740 and 1750 may be separate instruments. Alternatively, some or all of them may be combined as a single instrument operating in a multistreaming or a multiplexed mode.

EXAMPLE 12

(The invention controlling paraxylene production process)

Figure 12:
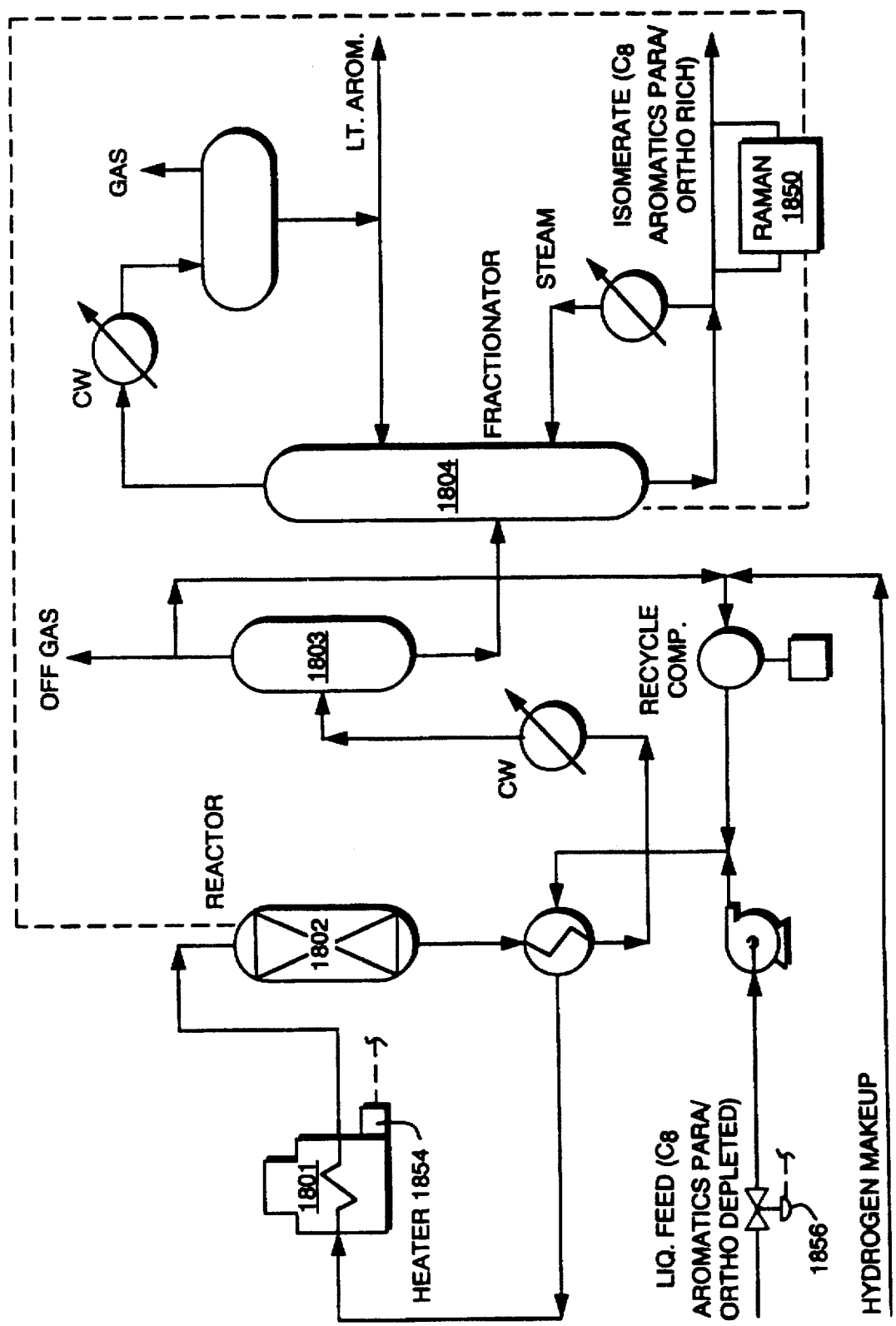
FIG. 12 illustrates schematically an embodiment in which the para-xylene production process of Example 12 is controlled.

Referring to FIG. 12, para-xylene can also be produced by selective isomerization of p-xylene-depleted, $C_8$ aromatics streams using a catalytic process that also converts ethylbenzene to benzene and non-aromatics to light paraffins. The operation of the unit is generally as described in *Hydrocarbon Processing Petrochemical Handbook*, March, 1993, p. 196. The feedstock is combined with hydrogen-rich recycle gas and makeup hydrogen, then heated by an effluent heat exchanger and Furnace 1801, then charged as a vapor to Reactor 1802 which contains a fixed-bed catalyst. The effluent, after cooling, goes to Separator 1803 which removes offgas for recycle. The remaining effluent is then fractionated in Fractionator 1804 to separate the para-enriched $C_8$ bottoms from light paraffins and aromatics. Raman spectrometer 1850 is used to measure product composition (i.e., concentration of ortho-, meta- and para-xylene) and is used for feedback control of Reactor 1802 and/or Fractionator 1804.

EXAMPLE 13

(The invention controlling an ethylbenzene production process)

Figure 13:
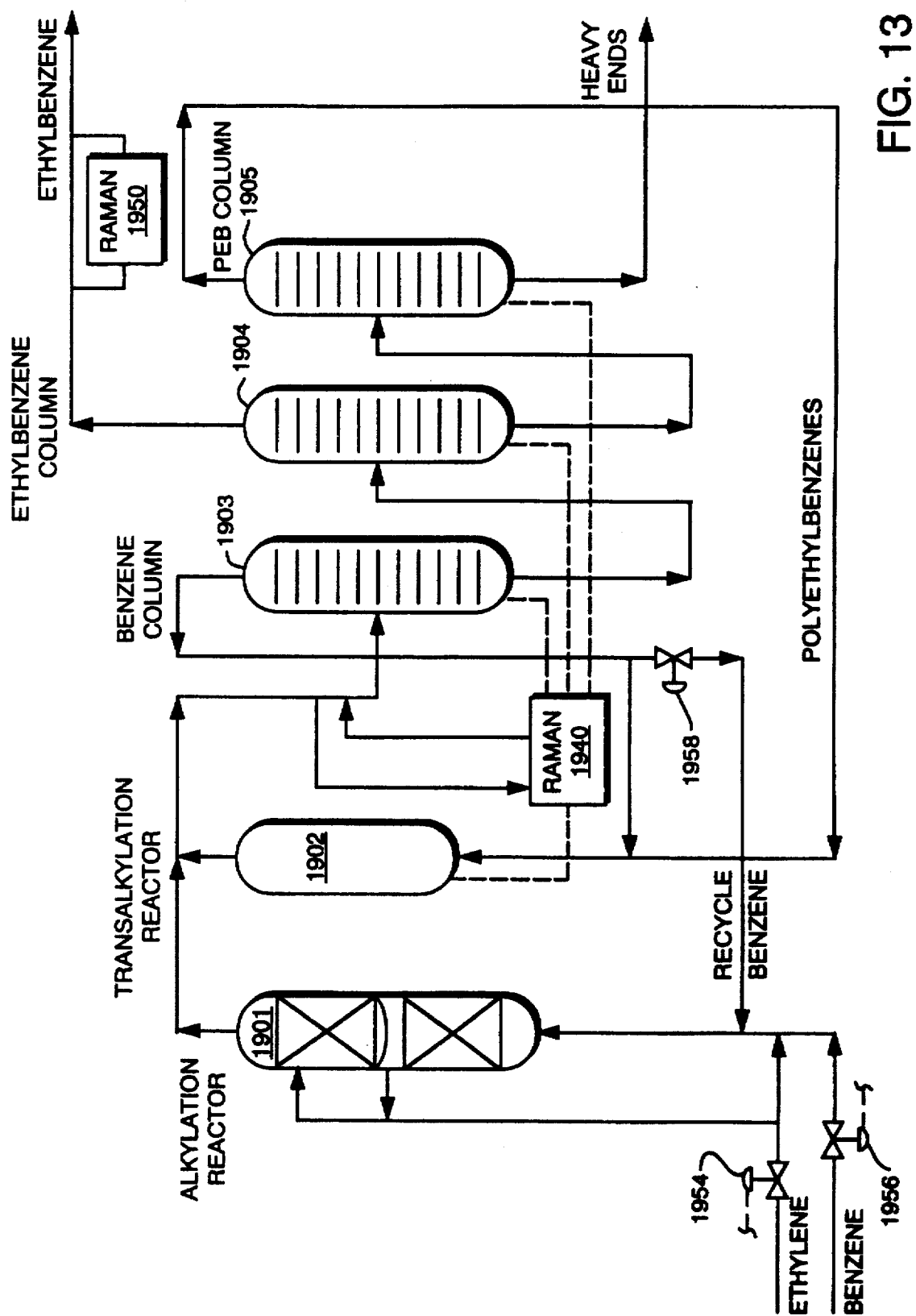
FIG. 13 illustrates schematically an embodiment in which the ethylbenzene production process of Example 13 is controlled.

Benzene may be alkylated with ethylene to produce ethylbenzene using a fixed-bed, zeolite catalyst. The operation of the unit is illustrated in FIG. 13 and is generally as described in *Hydrocarbon Processing Petrochemical Handbook*, March, 1993, p. 178. Fresh and recycle benzene are combined with ethylene and charged to Reactor 1901 to produce the products, leaving an excess of benzene. The effluent is fractionated using three columns (designated by their overhead fractions): Recycle Benzene Column 1903, Ethylbenzene Column 1904, and Polyethylbenzene (PEB) Column 1905. The polyethylbenzenes are mixed with a recycle benzene slip stream and charged to Transalkylation Reactor 1902 to produce more ethylbenzene. The transalkylation effluent is recombined with the effluent from Reactor 1901 and refractionated. Insignificant amounts of xylene and other byproducts are produced.

Raman spectrometer 1940 can be used for feed-forward control of the temperatures and other conditions in Columns 1903, 1904 and 1905 to optimize the fractionation of the combined effluent from the reactors. Alternatively or additionally, Raman spectrometer 1940 can provide feedback control to Transalkylation Reactor 1902, based on the PEB concentration in the effluent. Raman spectrometer 1950 monitors product purity.

Raman spectrometers 1940 and 1950 may be separate instruments. Alternatively, they may be combined as a single instrument operating in a multistreaming or a multiplexed mode.

EXAMPLE 14

(The invention controlling xylene isomers production process)

Figure 14:
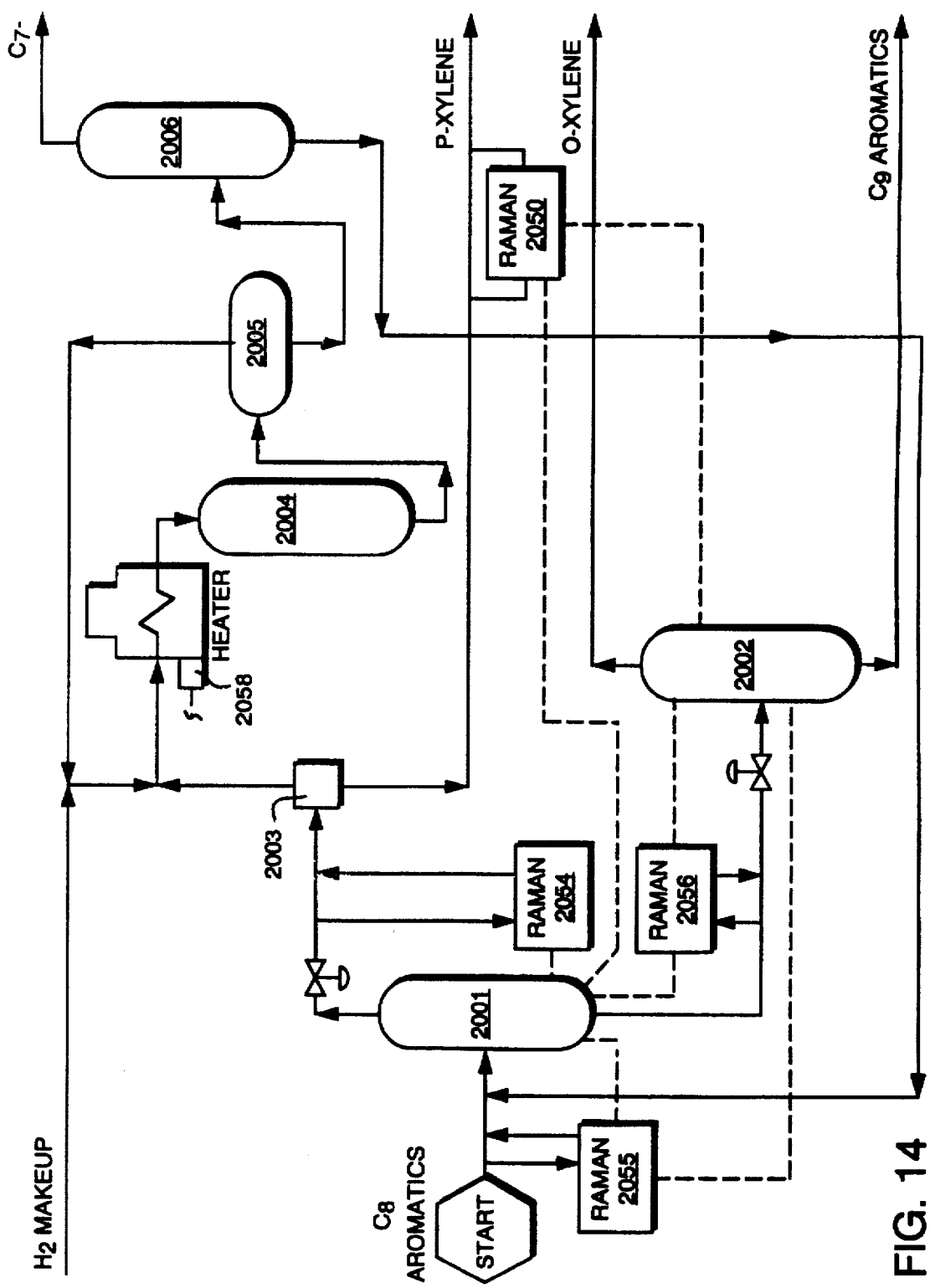
FIG. 14 illustrates schematically an embodiment in which the xylene isomers production process of Example 14 is controlled.

This process, illustrated in FIG. 14, is designed to produce 99+% pure ortho- and para-xylene isomers from a mixture of $C_8$ aromatics. The operation of the unit is generally as described in *Hydrocarbon Processing Petrochemical Handbook*, March, 1993, p. 215. The feedstock is first fed to Xylene Splitter 2001 which separates an overhead fraction from which meta and para isomers can be isolated, and a bottom fraction from which the ortho isomer is isolated. At this point the process is split into two nearly separate sub-processes.

A UOP Parex® process unit 2003 isolates nearly pure paraxylene from the overhead fraction of Xylene Splitter 2001. High-purity meta-xylene may also be isolated at this point using a separate process (e.g., MX Sorbex®). The remainder of the overhead fraction is then reheated and directed to Reactor 2004, which catalytically converts it into an equilibrium $C_8$ aromatic isomer mixture (using hydrogen from recycle gas and makeup). Hydrogen-rich recycle gas is removed from the effluent in Separator 2005. Light products are removed in Fractionator 2006. After removal of these fractions, the $C_8$ equilibrium mixture is recycled and combined with fresh feed. Raman spectrometer 2054 provides feed-forward control to process unit 2003, based on the composition of overhead from Splitter 2001.

The bottoms from Xylene Splitter 2001 are directed to Splitter 2002 which separates ortho-xylene as overhead and a heavy (C9+) bottom fraction. Purity of the ortho-xylene depends on fractionator efficiency and feed composition. Feedback control based on ortho-xylene purity determination by Raman spectrometer 2050, combined with feed-forward control based on feed purity determination by Raman spectrometer 2055, can optimize the efficiency of Splitter 2001 and/or 2002. Raman spectrometer 2054 and/or Raman spectrometer 2056 can provide feedback control to Splitter 2001, based on the proportions of ortho, meta and para isomer in each stream. Raman spectrometer 2056 provides feedforward control to Splitter 2002.

Raman spectrometers 2050, 2054, 2055 and 2056 may be separate instruments. Alternatively, some or all of them may be combined as a single instrument operating in a multi-streaming or a multiplexed mode.

EXAMPLE 15

(The invention controlling a dimethyl terephthalate production process)

Figure 15:
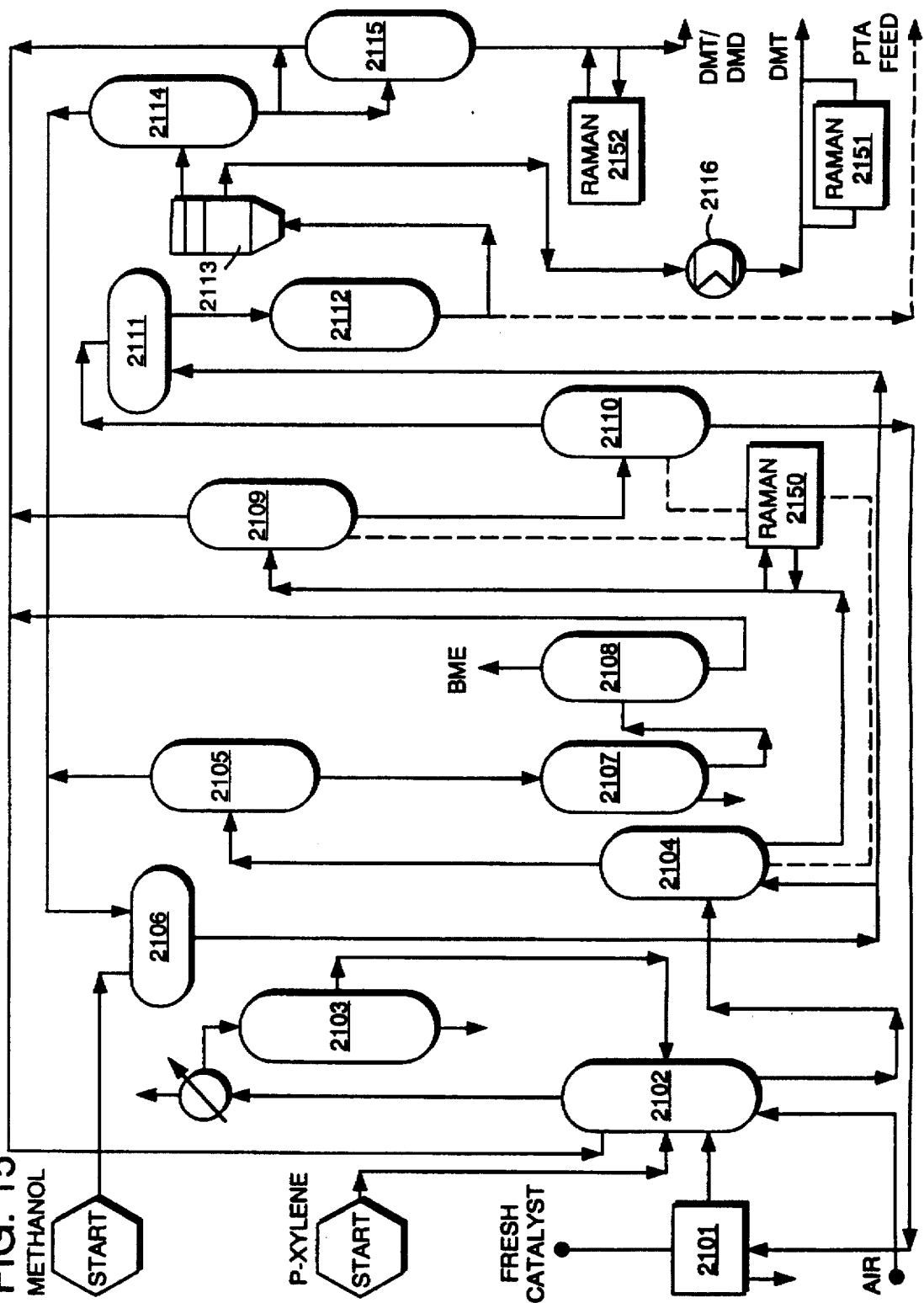
FIG. 15 illustrates schematically an embodiment in which the dimethyl terephthalate production process of Example 15 is controlled.

This process produces dimethyl terephthalate (DMT) from p-xylene and methanol, by catalytic oxidation followed by esterification. The operation of the unit is illustrated in FIG. 15 and is generally as described in *Hydrocarbon Processing Petrochemical Handbook*, March, 1993, p. 176. Para-xylene and recycled p-methyl toluate are continuously oxidized in Oxidizer 2102 using a heavy metal catalyst supplied from Vessel 2101. The oxidate, consisting of p-toluic acid and monomethyl terephthlate, is esterified under high pressure in Esterifier 2104, using methanol from Holding Tank 2106, to yield a mixture of DMT and p-methyl toluate. Overhead methanol from the esterification mixture is distilled in Still 2105 and recycled to Holding Tank 2106. Bottoms from Esterifier 2104 are distilled in Column 2109 to obtain p-methyl toluate as overhead for recycle to Oxidizer 2102. Bottoms from Column 2109 are redistilled in Column 2110 to separate Crude DMT as overhead from residue bottoms. The residue bottoms are recycled to Catalyst Vessel 2101. The crude DMT overhead is recrystallized from methanol. Fiber grade DMT is separated in Centrifuges 2113, and the mother liquor redistilled for recycle of the methanol to Holding tank 2106. Undistilled byproducts are purged to remove residual methanol in Stripper 2115. Fiber grade DMT from Centrifuges 2106 is heated in Extruder 2116 and can be transported or directed to other units in molten form.

Raman spectrometer 2150 is used to monitor the esterification mixture after removal of the methanol, for feedback control of Esterifier 2104 and/or for feed-forward control of columns 2109 and 2110. Raman spectrometer 2151 monitors the purity of the DMT product. Raman spectrometer 2152 is used to monitor the composition of byproducts separated from the DMT by recrystallization. Raman spectrometers 2050, 2051 and 2152 may be separate instruments. Alternatively, some or all of them may be combined as a single instrument operating in a multistreaming or a multiplexed mode.

EXAMPLE 16

(The invention controlling styrene production process)

Figure 16:
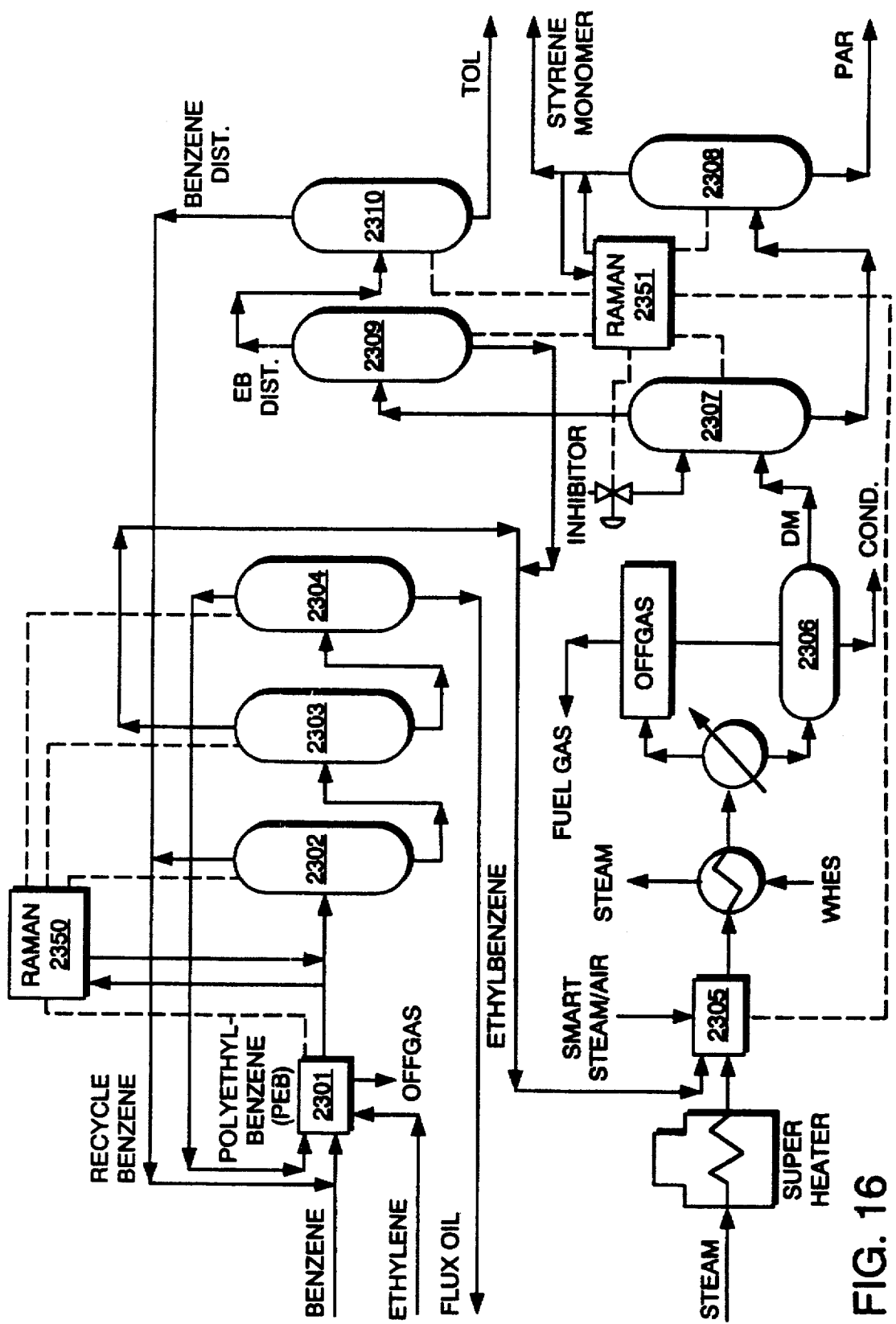
FIG. 16 illustrates schematically an embodiment in which the styrene process, as described of Example 16, is controlled.

Styrene is produced by catalytic alkylation of benzene with ethylene, followed by dehydrogenation of the ethylbenzene (EB) product to form styrene. The operation of the unit is illustrated in FIG. 16 and is generally as described in *Hydrocarbon Processing Petrochemical Handbook*, March, 1993, p. 212. Ethylene is charged with fresh and recycle benzene into Reactor 2301, which consists of two stages. In this reactor, polyalkylation occurs along with EB formation, but the polyethylbenzenes (PEB) are subsequently transalkylated to EB with excess benzene. The product mixture is fractionated using three columns, each designated by their overhead fractions: Benzene column 2302, EB column 2303, and PEB column 3204. Benzene from column 2302 is recycled. Overhead from PEB column 2304 is recycled to Reactor 2301 for transalkylation, while the high-boiling bottoms from this column are collected as Flux Oil. The EB from column 2303 is charged to multistage Dehydrogenator 2305, where dehydrogenation to styrene takes place, under vacuum and in the presence of steam. After removal of process condensate and addition of polymerization inhibitor, the crude styrene is purified in columns 2307 and 2308. Column 2307 removes unconverted EB as overhead, and the overhead is distilled in column 2309 to obtain EB bottoms for recycle, and an overhead which is distilled in column 23 10 to yield recycle benzene as overhead and a small amount of toluene as bottoms. Finally, bottoms from column 2307 are distilled in column 2308 to yield purified styrene monomer as overhead and tarry bottoms.

Raman spectrometer 2350 is used for feedback control of Reactor 2301 and/or for feed-forward control of columns 2302, 2303 and 2304, based on Raman spectra determinations of polyethylbenzene which must be separated and recycled for transalkylation. Raman spectrometer 2351 is used to monitor the product composition, for feedback control of dehydrogenator 2305 based on Raman spectra determinations of unconverted ethylbenzene. Raman spectrometer 2351 may also be used for feedback control of inhibitor addition. Feed-forward control of distillations in columns 2307, 2308, 2309 and 2310 is also possible using Raman spectrometer 2351.

Raman spectrometer 2350 and Raman spectrometer 2351 may be separate instruments or a single instrument operating in a multistreaming or a multiplexing mode.

EXAMPLE 17

(Comparative with Species Analysis Using Conventional Gas Liquid Chromatography)

Figure 17:
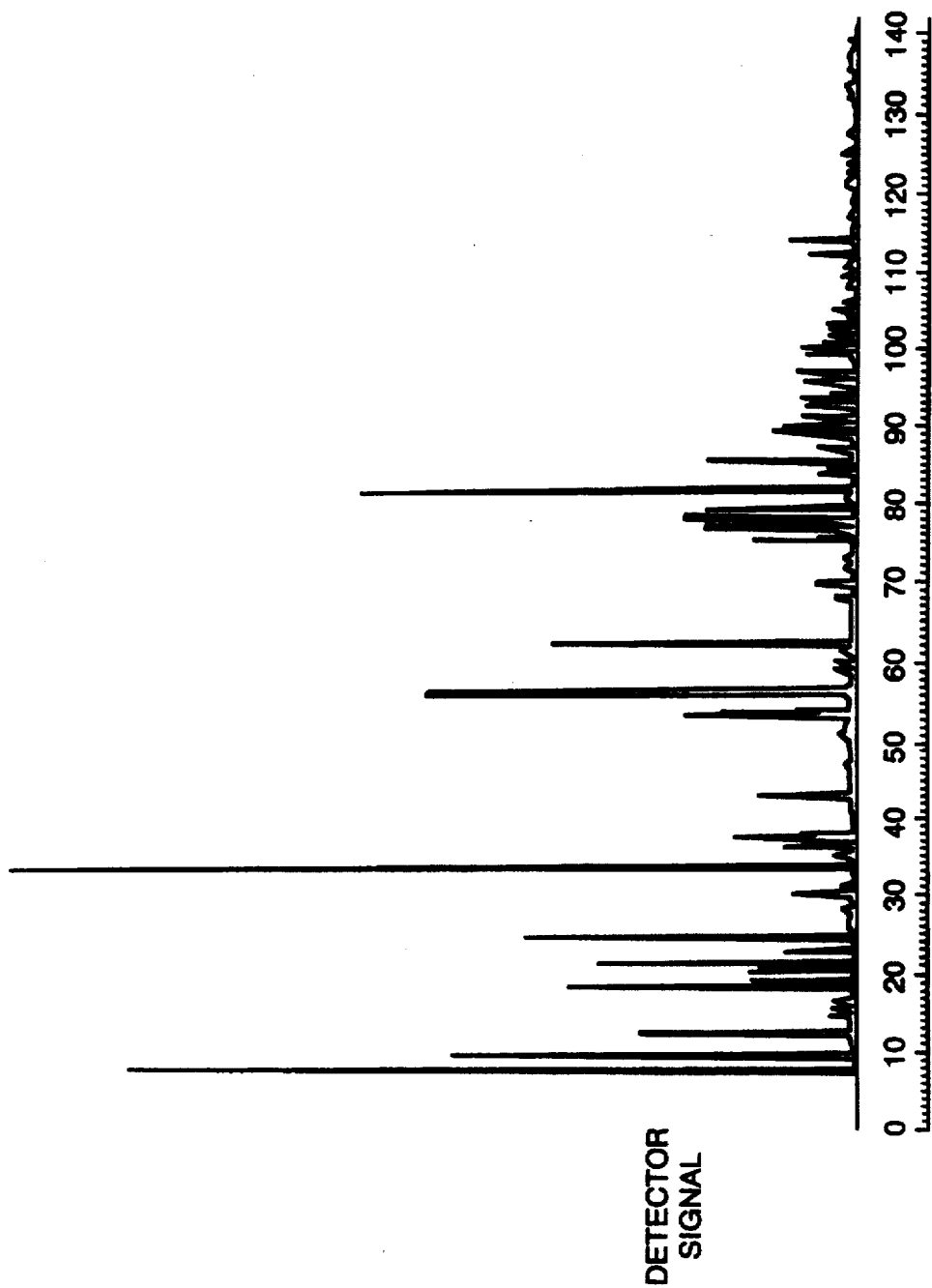
FIG. 17 illustrates a typical chromatogram used for PIANO analysis of a reformate by the prior art chromatographic technique of Example 17, with detector signal plotted on the vertical axis as a function of time (in minutes) on the horizontal axis.

The chromatogram for a reformate, shown in FIG. 17, was obtained using a Hewlett Packard Model 5890 temperature programmed gas chromatograph with a flame ionization detector and a Supelco Petrocol DH capillary column (fused silica, 100M×0.25 mm i.d., df=0.5 uM). Chromatographic conditions were adjusted according to the standard methods established by the instrument manufacturer and Analytical Automation Specialists, Inc. This prior art method is useful for the determination of individual species as well as compound types, and can serve as the primary method for calibration of the near infrared instruments used in the present invention. However, as shown by the time elapse in FIG. 17, this method is slow; FIG. 17 shows an elutriation time for the last fractions of 142 min or over two hours. The PIANO method is thus seen to be too slow for efficient use in closed loop control for many refinery processes.

EXAMPLE 18

(Illustration of Raman Spectra for Aromatic Species of Interest)

Figure 18:
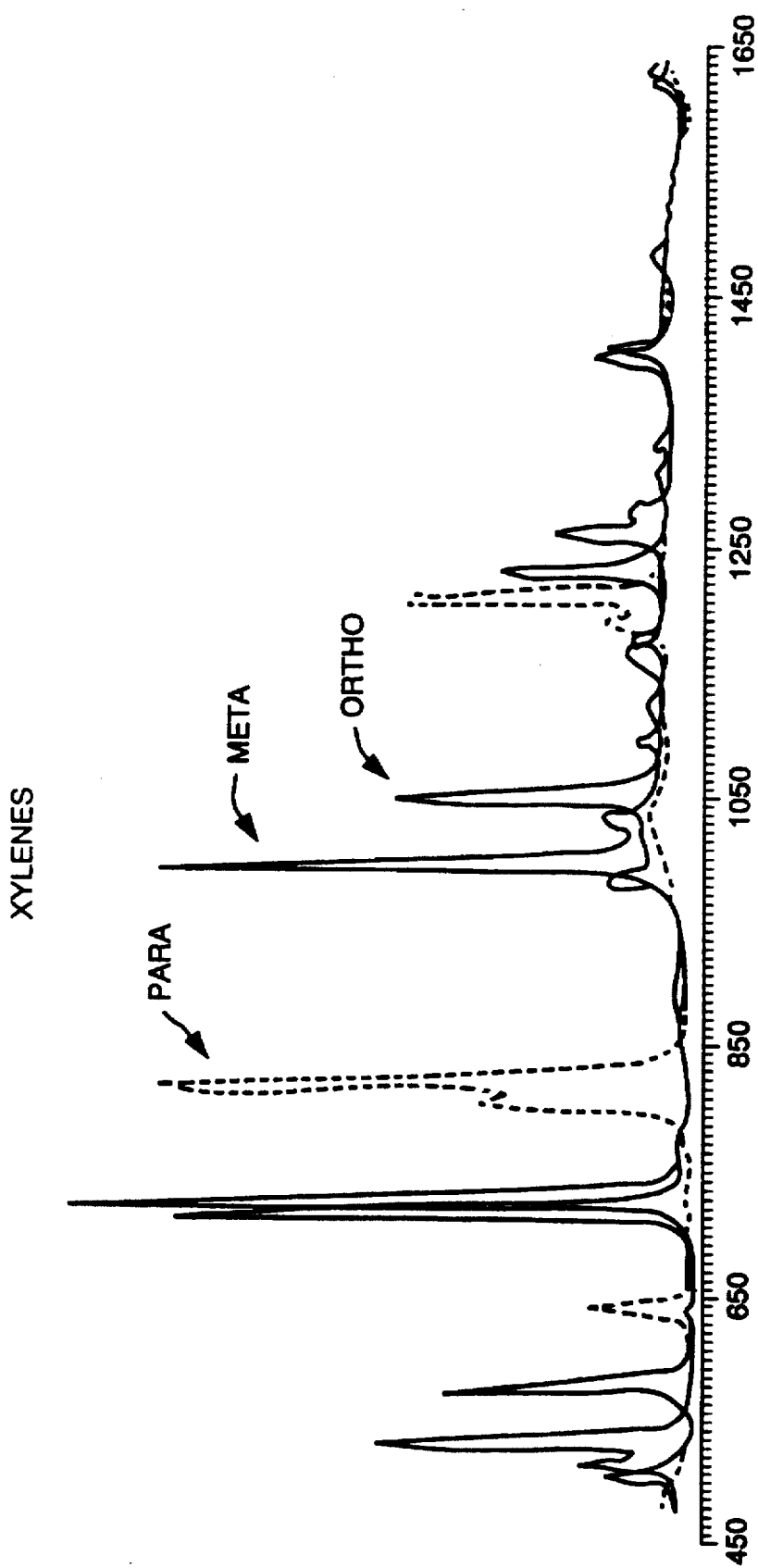
FIG. 18 contains three overlaid Raman spectra for ortho-, meta-, and para-xylene.
Figure 19:
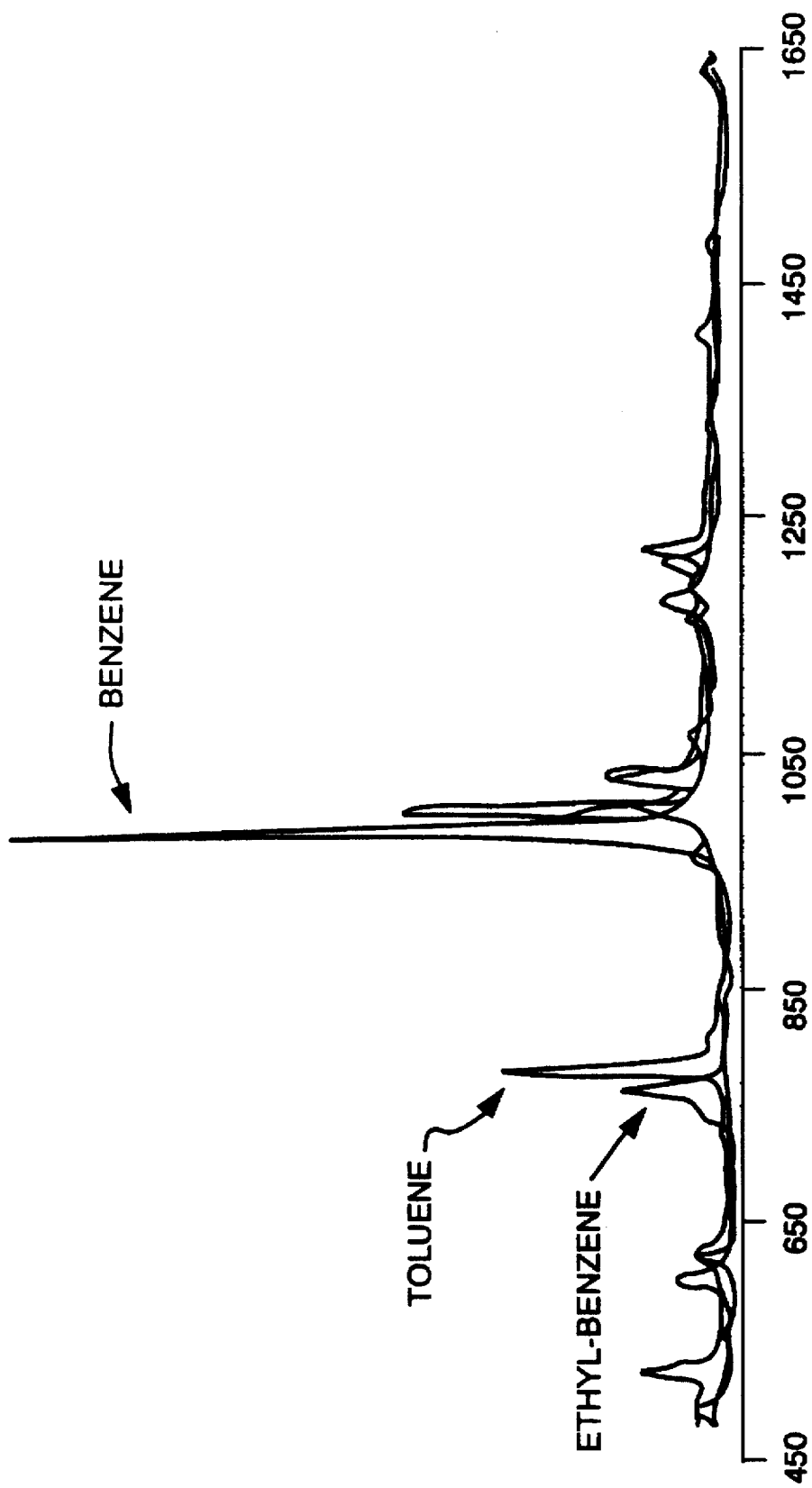
FIG. 19 contains three overlaid Raman spectra for benzene, toluene, and ethylbenzene.
Figure 20:
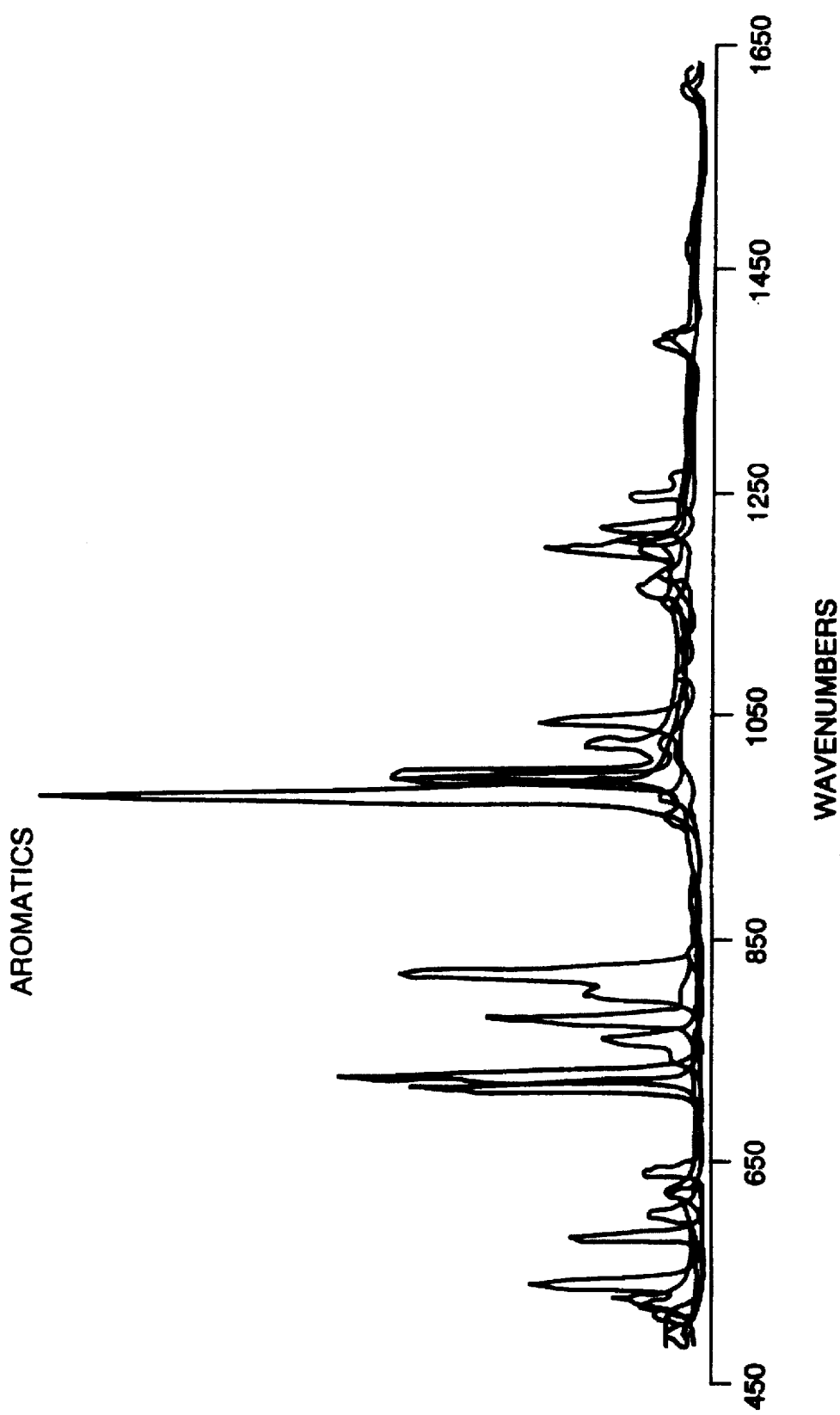
FIG. 20 contains six overlaid Raman spectra for benzene, toluene, ethylbenzene, ortho-xylene, meta-xylene and para-xylene.

FIG. 18 contains overlaid Raman spectra for the three isomers of xylene. Likewise, FIG. 19 contains spectra for benzene, toluene and ethylbenzene. FIG. 20 contains the overlaid Raman spectra for all six of the compounds. These spectra were obtained using the dispersive Raman spectrometer described in Example 1. The spectra show that there are sharp Raman bands that are specific to each compound.

Modifications

Though fundamental bands have been recited, overtones and derivatives of both overtones and fundamental bands may sometimes be substituted if of sufficient strength. This invention can control other refinery and chemical process units, e.g., isomerization, alky, and MTBE.

Specific compositions, methods, or embodiments discussed are intended to be only illustrative of the invention disclosed by this specification. Variations on these compositions, methods, or embodiments are readily apparent to a person of skill in the art based upon the teachings of this specification and are therefore intended to be included as part of the inventions disclosed herein.

Reference to documents made in the specification is intended to result in such patents or literature being expressly incorporated herein by reference.

What is claimed is:

1. A process comprising
   a) irradiating a sample of a mixture of two or more liquids comprising one or more substituted aromatic hydrocarbons and/or benzene to produce scattered Raman radiation emitted from the sample;
   b) collecting Raman scattered radiation emitted from the sample;
   c) dispersing or transforming the collected Raman scattered radiation from the sample into sample spectra with intensities corresponding to the chemical composition of components of the mixture of said sample and concentration of said components;
   d) deriving a regression model by multivariate analysis of known Raman spectra, or mathematical function of known Raman spectra, of liquid mixtures containing known concentrations of substituted aromatic hydrocarbons, and/or benzene;
   e) processing said sample spectra according to said regression model to produce a control signal representative of the concentration in said mixture of one or more of the substituted aromatic hydrocarbons and/or benzene;
   f) controlling a process in response to said control signal.

2. The process of claim 1 wherein the liquid mixture is a hydrocarbon mixture and the sample is irradiated with near infrared radiation.

3. The process of claim 2 wherein the substituted aromatic hydrocarbon comprises toluene, ethylbenzene, ortho-xylene, meta-xylene, and/or para-xylene.

4. The process of claim 1 wherein the sample comprises ortho-xylene.

5. The process of claim 1 wherein the sample comprises meta-xylene.

6. The process of claim 1 wherein the sample comprises para-xylene.

7. The process of claim 1 wherein the sample comprises toluene.

8. The process of claim 1 wherein the process controlled is a reforming process.

9. The process of claim 1 wherein the process controlled is an aromatic extraction process.

10. The process of claim 1 wherein the process controlled is a distillation process.

11. The process of claim 1 wherein the process controlled is a fractionation process.

12. The process of claim 1 wherein the process controlled is a process for producing toluene.

13. The process of claim 1 wherein the process controlled is an aromatic disproportionation process.

14. The process of claim 1 wherein the process controlled is a process for the fractionation of benzene, toluene, and xylene.

15. The process of claim 1 wherein the process controlled is a process for producing cumene.

16. The process of claim 1 wherein the process controlled is a process for producing cyclohexane from benzene.

17. The process of claim 1 wherein the process controlled is a process for producing para-xylene.

18. The process of claim 1 wherein the process controlled is a process for producing ethylbenzene.

19. The process of claim 1 wherein the process controlled is a process for producing and/or separating xylene isomers.

20. The process of claim 1 wherein the process controlled is a process for the production of dimethyl terephthalate.

21. The process of claim 1 wherein the dispersed or transformed spectra processed is a spectral region selected from 1080–940 $cm^{-1}$, 810–680 $cm^{-1}$, 620–470 $cm^{-1}$, 1860–184 $cm^{-1}$, 3600–2250 $cm^{-1}$, or some combination of these spectral regions.

22. The process of claim 1 wherein the dispersed or transformed spectra processed is a spectral region selected from 1090–1020 $cm^{-1}$, 790–670 $cm^{-1}$, 630–550 $cm^{-1}$, 1860–184 $cm^{-1}$, 3600–2250 $cm^{-1}$, or some combination of these spectral regions.

23. The process of claim 1 wherein the dispersed or transformed spectra processed is a spectral region selected from 1260–1120 $cm^{-1}$, 900–750 $cm^{-1}$, 520–420 $cm^{-1}$, 1860–184 $cm^{-1}$, 3600–2250 $cm^{-1}$, or some combination of these spectral regions.

24. The process of claim 1 wherein the dispersed or transformed spectra processed is a spectral region selected from 1208–1166 $cm^{-1}$, 1012–956 $cm^{-1}$, 1860–184 $cm^{-1}$, 3600–2250 $cm^{-1}$, or some combination of these spectral regions.

25. The process of claim 1 wherein the dispersed or transformed spectra processed is a spectral region selected from 1245–1194 $cm^{-1}$, 1059–970 $cm^{-1}$, 803–714 $cm^{-1}$, 1860–184 $cm^{-1}$, 3600–2250 $cm^{-1}$, or some combination of these spectral regions.

26. The process of claim 1 wherein the dispersed or transformed spectra processed is a spectral region selected from 1240–1155 cm$^{-1}$, 1620–1494 cm$^{-1}$, 794–717 cm$^{-1}$, 1057–900 cm$^{-1}$, 1860–184 cm$^{-1}$, 3600–2250 cm$^{-1}$, or some combination of these spectral regions.

27. The process of claim 1 wherein the dispersed or transformed spectra processed is a spectral region selected from 1670–1600 cm$^{-1}$, 1500–1450 cm$^{-1}$, 1070–1050 cm$^{-1}$, 1010–960 cm$^{-1}$, 1860–184 cm$^{-1}$, 3600–2250 cm$^{-1}$, or some combination of these spectral regions.

28. The process of claim 1 wherein the dispersed or transformed spectra processed is a spectral region selected from 1245–1133 cm$^{-1}$, 1082–989 cm$^{-1}$, 849–760 cm$^{-1}$, 640–593 cm$^{-1}$, 570–505 cm$^{-1}$, 1860–184 cm$^{-1}$, 3600–2250 cm$^{-1}$, or some combination of these spectral regions.

29. The process of claim 1 wherein said multivariate analysis comprises PLS.

30. A process comprising
   a) irradiating a sample of a liquid mixture comprising benzene with near infrared radiation, producing scattered Raman radiation emitted from the sample;
   b) collecting Raman scattered radiation emitted from the sample;
   c) dispersing or transforming the collected Raman scattered radiation from the sample into spectra with intensities corresponding to the chemical composition of the components of the mixture of said sample and concentration of said components;
   d) processing said spectra according to a regression model derived by multivariate analysis of Raman spectra, or mathematical function thereof, of liquid mixtures containing known concentrations of benzene, and producing a control signal representative of the concentration in said mixture of benzene;
   e) controlling a process in response to said control signal.

31. The process of claim 30 wherein the liquid mixture is a hydrocarbon mixture.

32. A process comprising
   a) preparing multiple samples of liquid mixtures each comprising one or more substituted aromatic hydrocarbons or benzene in varying concentrations;
   b) irradiating the respective samples of said mixtures individually with near infrared radiation, producing scattered Raman radiation emitted from each sample;
   c) collecting Raman scattered radiation emitted from the respective aromatic hydrocarbon- or benzene-containing samples;
   d) dispersing or transforming the collected Raman scattered radiation from the samples into spectra with intensities corresponding to the chemical composition of the components of the mixtures of said samples and concentration of said components;
   e) performing multivariate analysis on said spectra, or mathematical functions thereof, to derive a regression model representative of mixtures containing one or more substituted aromatic hydrocarbons or benzene.

33. The process of claim 32 wherein the substituted aromatic hydrocarbon is a xylene.

34. The process of claim 32 wherein the substituted aromatic hydrocarbon is ethylbenzene.

35. The process of claim 32 wherein the substituted aromatic hydrocarbon is styrene.

36. The process of claim 32 wherein the substituted aromatic hydrocarbon is cumene.

37. The process of claim 32 wherein the samples comprise benzene.

38. The process of claim 32 wherein the liquid mixture comprises a synthetic petroleum mixture.

39. A process comprising
   a) recovering multiple samples of liquid mixture each comprising one or more substituted aromatic hydrocarbons or benzene in varying concentrations;
   b) analyzing at least a portion of the samples to determine the components therein and their concentrations;
   c) irradiating the respective samples of said mixtures individually with near infrared radiation, producing scattered Raman radiation emitted from each sample mixture;
   d) collecting Raman scattered radiation emitted from the respective aromatic hydrocarbon- or benzene-containing samples;
   e) dispersing or transforming the collected Raman scattered radiation from the samples into spectra with intensities corresponding to the chemical composition of the components of the mixtures of said samples and concentration of said components;
   f) performing multivariate analysis on said spectra or mathematical functions thereof to derive a regression model representative of mixtures containing one or more substituted aromatic hydrocarbons or benzene.

40. The process of claim 39 wherein the liquid mixture comprises a petroleum mixture.

41. The process of claim 39 wherein the substituted aromatic hydrocarbon, is a xylene.

42. The process of claim 39 wherein the substituted aromatic hydrocarbon is ethylbenzene.

43. The process of claim 39 wherein the substituted aromatic hydrocarbon is styrene.

44. The process of claim 39 wherein the substituted aromatic hydrocarbon is cumene.

45. The process of claim 39 wherein the samples comprise benzene.

46. The process of claim 39 wherein the liquid mixture comprises a synthetic petroleum mixture.

47. A process for determining the concentration of one or more xylenes in a liquid sample comprising
   a) irradiating a liquid sample containing one or more isomers of xylene with near infrared radiation, producing scattered Raman radiation emitted from said sample;
   b) collecting Raman scattered radiation emitted from the sample;
   c) transferring collected Raman scattered radiation and dispersing or transforming the collected Raman scattered radiation from the sample into spectra with intensities corresponding to the chemical composition of the components of said sample and concentrations of said components;
   d) determining the concentration of one or more xylenes present by processing the spectral intensities according to the model of claim 39, with the provision that the near infrared source radiation wavelength in this embodiment is the same as or is correlated to that employed in establishing said model.

48. A process for determining the concentration of benzene in a liquid sample comprising
   a) irradiating a liquid sample containing benzene with near infrared radiation, producing scattered Raman radiation emitted from said sample;
   b) collecting Raman scattered radiation emitted from the sample;

c) transferring collected Raman scattered radiation and dispersing or transforming the collected Raman scattered radiation from the sample into spectra with intensities corresponding to the chemical composition of the components of said sample and concentrations of said components;

d) determining the concentration of benzene present by processing the spectral intensities according to the model of claim 39, with the provision that the near infrared source radiation wavelength in this embodiment is the same as or is correlated to that employed in establishing said model.

49. The process of claim 48 wherein the liquid sample comprises a petroleum mixture.

50. A process comprising monitoring a process for the production of a liquid containing one or more xylenes by periodically or continuously a) irradiating a liquid sample of the process containing one or more isomers of xylene with near infrared radiation, producing scattered Raman radiation emitted from said sample;

b) collecting Raman scattered radiation emitted from the sample;

c) transferring collected Raman scattered radiation and dispersing or transforming the collected Raman scattered radiation from the sample into spectra with intensities corresponding to the chemical composition of the components of said sample and concentrations of said components;

d) determining the concentration of one or more xylenes present by processing the spectral intensities according to the model of claim 17, with the provision that the near infrared source radiation wavelength in this embodiment is the same as or is correlated to that employed in establishing said model;

e) controlling the parameters of the process to produce said liquid in response to the determined concentration of one or more xylenes in the liquid sample.

51. The process of claim 50 wherein the liquid comprises a petroleum mixture.

52. A process comprising a) recovering multiple samples of liquid mixture each comprising one or more substituted aromatic hydrocarbons or benzene in varying concentrations;

b) irradiating the respective samples of said mixtures individually with near infrared radiation, producing scattered Raman radiation emitted from each sample mixture;

c) analyzing at least a portion of the samples to determine the components therein and their concentrations;

d) collecting Raman scattered radiation emitted from the respective aromatic hydrocarbon- or benzene-containing samples;

e) dispersing or transforming the collected Raman scattered radiation from the samples into spectra with intensities corresponding to the chemical composition of the components of the mixtures of said samples and concentration of said components;

f) performing multivariate analysis on said spectra or mathematical functions thereof to derive a regression model representative of mixtures containing one or more substituted aromatic hydrocarbons or benzene.

53. The process of claim 52 wherein the liquid mixture comprises a petroleum mixture.

54. The process of claim 52 wherein the substituted aromatic hydrocarbon is a xylene.

55. The process of claim 52 wherein the substituted aromatic hydrocarbon is ethylbenzene.

56. The process of claim 52 wherein the substituted aromatic hydrocarbon is styrene.

57. The process of claim 52 wherein the substituted aromatic hydrocarbon is cumene.

58. The process of claim 52 wherein the samples comprise benzene.

59. The process of claim 52 wherein the liquid mixture comprises a synthetic petroleum mixture.

60. A process comprising a) preparing multiple samples of synthetic petroleum mixtures each comprising a mixture of paraffins, isoparaffins, aromatics, naphthenes, and olefins and one or more isomers of xylene in varying concentrations;

b) irradiating the respective samples of synthetic petroleum mixtures individually with near infrared radiation, producing scattered Raman radiation emitted from each sample mixture;

c) collecting Raman scattered radiation emitted from the respective petroleum samples;

d) dispersing or transforming the collected Raman scattered radiation from the samples into spectra with intensities corresponding to the chemical composition of the components of the mixtures of said samples and concentration of said components;

e) performing multivariate analysis on said spectra or mathematical functions thereof to derive a regression model representative of mixtures containing one or more xylenes.

61. A process for fuel blending comprising a) irradiating multiple samples of liquid mixtures each comprising one or more substituted aromatic hydrocarbons or benzene with near infrared radiation, producing scattered Raman radiation emitted from each sample mixture;

b) collecting Raman scattered radiation emitted from the respective samples;

c) dispersing or transforming the collected Raman scattered radiation from the samples into spectra with intensities corresponding to the chemical composition of the components of the mixtures of said samples and concentration of said components;

d) processing said spectra according to a regression model derived by multivariate analysis of Raman spectra, or mathematical function thereof, of liquid mixtures containing known concentrations of one or more substituted aromatic hydrocarbons or benzene, and outputting a periodic, intermittent or continuous signal indicative of the content of a substituted aromatic hydrocarbon or benzene;

e) inputting said signal to a means for controlling a fuel blending process.

62. A process comprising a) irradiating a sample of a liquid mixture comprising one or more substituted aromatic hydrocarbons with visible or ultraviolet radiation, producing scattered Raman radiation emitted from the sample;

b) collecting Raman scattered radiation emitted from the sample;

c) dispersing or transforming the collected Raman scattered radiation from the sample into spectra with intensities corresponding to the chemical composition of the components of the mixture of said sample and concentration of said components;

d) processing said spectra according to a regression model derived by multivariate analysis of Raman spectra, or mathematical function thereof, of liquid mixtures containing known concentrations of substituted aromatic hydrocarbons, and producing a control signal representative of the concentration in said mixture of one or more substituted hydrocarbons;

e) controlling a process in response to said control signal.

63. A process comprising a) irradiating a sample of a liquid mixture comprising benzene with visible or ultraviolet radiation, producing scattered Raman radiation emitted from the sample;

b) collecting Raman scattered radiation emitted from the sample;

c) dispersing or transforming the collected Raman scattered radiation from the sample into spectra with intensities corresponding to the chemical composition of the components of the mixture of said sample and concentration of said components;

d) processing said spectra according to a regression model derived by multivariate analysis of Raman spectra, or mathematical function thereof, of liquid mixtures containing known concentrations of benzene, and producing a control signal representative of the concentration in said mixture of benzene;

e) controlling a process in response to said control signal.

64. A process comprising a) preparing multiple samples of liquid mixtures each comprising one or more substituted aromatic hydrocarbons or benzene in varying concentrations;

b) irradiating the respective samples of said mixtures individually with visible or ultraviolet radiation, producing scattered Raman radiation emitted from each sample;

c) collecting Raman scattered radiation emitted from the respective aromatic hydrocarbon- or benzene-containing samples;

d) dispersing or transforming the collected Raman scattered radiation from the samples into spectra with intensities corresponding to the chemical composition of the components of the mixtures of said samples and concentration of said components;

e) performing multivariate analysis on said spectra, or mathematical functions thereof, to derive a regression model representative of mixtures containing one or more substituted aromatic hydrocarbons or benzene.

65. A process comprising a) recovering multiple samples of liquid mixture each comprising one or more substituted aromatic hydrocarbons or benzene in varying concentrations;

b) analyzing at least a portion of the samples to determine the components therein and their concentrations;

c) irradiating the respective samples of said mixtures individually with visible or ultraviolet radiation, producing scattered Raman radiation emitted from each sample mixture;

d) collecting Raman scattered radiation emitted from the respective aromatic hydrocarbon- or benzene-containing samples;

e) dispersing or transforming the collected Raman scattered radiation from the samples into spectra with intensities corresponding to the chemical composition of the components of the mixtures of said samples and concentration of said components;

f) performing multivariate analysis on said spectra or mathematical functions thereof to derive a regression model representative of mixtures containing one or more substituted aromatic hydrocarbons or benzene.

66. A process comprising a) recovering multiple samples of liquid mixture each comprising one or more substituted aromatic hydrocarbons or benzene in varying concentrations;

b) irradiating the respective samples of said mixtures individually with visible or ultraviolet radiation, producing scattered Raman radiation emitted from each sample mixture;

c) analyzing at least a portion of the samples to determine the components therein and their concentrations;

d) collecting Raman scattered radiation emitted from the respective aromatic hydrocarbon- or benzene-containing samples;

e) dispersing or transforming the collected Raman scattered radiation from the samples into spectra with intensities corresponding to the chemical composition of the components of the mixtures of said samples and concentration of said components;

f) performing multivariate analysis on said spectra or mathematical functions thereof to derive a regression model representative of mixtures containing one or more substituted aromatic hydrocarbons or benzene.

* * * * *